(12) United States Patent
Pillay et al.

(10) Patent No.: US 10,478,527 B2
(45) Date of Patent: Nov. 19, 2019

(54) BIODEGRADABLE IMPLANT

(71) Applicant: UNIVERSITY OF THE WITWATERSRAND, JOHANNESBURG, Johannesburg, Gauteng (ZA)

(72) Inventors: Viness Pillay, Gauteng (ZA); Yahya Essop Choonara, Gauteng (ZA); Pradeep Kumar, Gauteng (ZA); Lisa Claire Du Toit, Johannesburg (ZA); Poornima Ramburrun, Gauteng (ZA)

(73) Assignee: University of the Witwatersrand, Johannesburg, Johannesburg, Gauteng (ZA)

( * ) Notice: Subject to any disclaimer, the term of this patent is extended or adjusted under 35 U.S.C. 154(b) by 0 days.

(21) Appl. No.: 15/757,475

(22) PCT Filed: Sep. 5, 2016

(86) PCT No.: PCT/IB2016/055301
§ 371 (c)(1),
(2) Date: Mar. 5, 2018

(87) PCT Pub. No.: WO2017/037685
PCT Pub. Date: Mar. 9, 2017

(65) Prior Publication Data
US 2019/0022281 A1   Jan. 24, 2019

(30) Foreign Application Priority Data

Sep. 4, 2015 (ZA) .................. 2015/06544

(51) Int. Cl.
*A61L 27/48* (2006.01)
*A61L 27/16* (2006.01)
*A61L 27/20* (2006.01)
*A61L 27/52* (2006.01)
*A61L 27/54* (2006.01)
*A61L 27/58* (2006.01)
*A61L 27/56* (2006.01)

(52) U.S. Cl.
CPC .............. *A61L 27/48* (2013.01); *A61L 27/16* (2013.01); *A61L 27/20* (2013.01); *A61L 27/52* (2013.01); *A61L 27/54* (2013.01); *A61L 27/56* (2013.01); *A61L 27/58* (2013.01); *A61L 2400/12* (2013.01); *A61L 2430/32* (2013.01)

(58) Field of Classification Search
CPC .......... A61L 27/48; A61L 27/16; A61L 27/20; A61L 27/52; A61L 27/54; A61L 27/56; A61L 27/58
See application file for complete search history.

(56) References Cited

U.S. PATENT DOCUMENTS

2006/0110429 A1* 5/2006 Reiff .................. A61F 9/0017
424/427

FOREIGN PATENT DOCUMENTS

WO    WO 2014/013188 A1    1/2014

OTHER PUBLICATIONS

Xie et al. (Microsurgery 28:471-479, 2008).*
Ramburrun Poornima et al, "Design of chitospheres loaded with pristine polymer particles for extended drug delivery via polyelectrolyte complexation and particulate leaching," International Journal of Pharmaceutics, vol. 479. No. 1, Feb. 1, 2015 (Feb. 1, 2015), pp. 189-206.
International Search Report of PCT International Patent Application No. PCT/IB2016/055301, dated Dec. 15, 2016, 3 pages.
Written Opinion of the International Searching Authority of PCT International Patent Application No. PCT/IB2016/055301, dated Dec. 15, 2016, 5 pages.

* cited by examiner

*Primary Examiner* — Shirley V Gembeh
(74) *Attorney, Agent, or Firm* — McDonnell Boehnen Hulbert & Berghoff LLP

(57) ABSTRACT

This invention relates to biodegradable implants comprising a hydrogel carrier matrix having dispersed therein a multitude of particles, wherein each of the multitude of particles and/or the hydrogel carrier matrix includes an active pharmaceutical ingredient (API) for the treatment of transected peripheral nerve injuries. Each of the multitude of particles and/or the hydrogel carrier matrix includes pristine polymer particles, preferably the pristine polymer particles may be polymethylmethacrylate polymers and derivatives thereof, preferably poly(methacrylic-co-methyl methacrylate) (PMMA). The spheroidal particles may each be formed from an outer shell including a chitosan (CHT) poly(methacrylic-co-methyl methacrylate) (PMMA) polyelectrolyte complex (CHT-PMMA-PEC) and an inner core including crosslinked chitosan having dispersed therein PMMA nanoparticles.

13 Claims, 17 Drawing Sheets

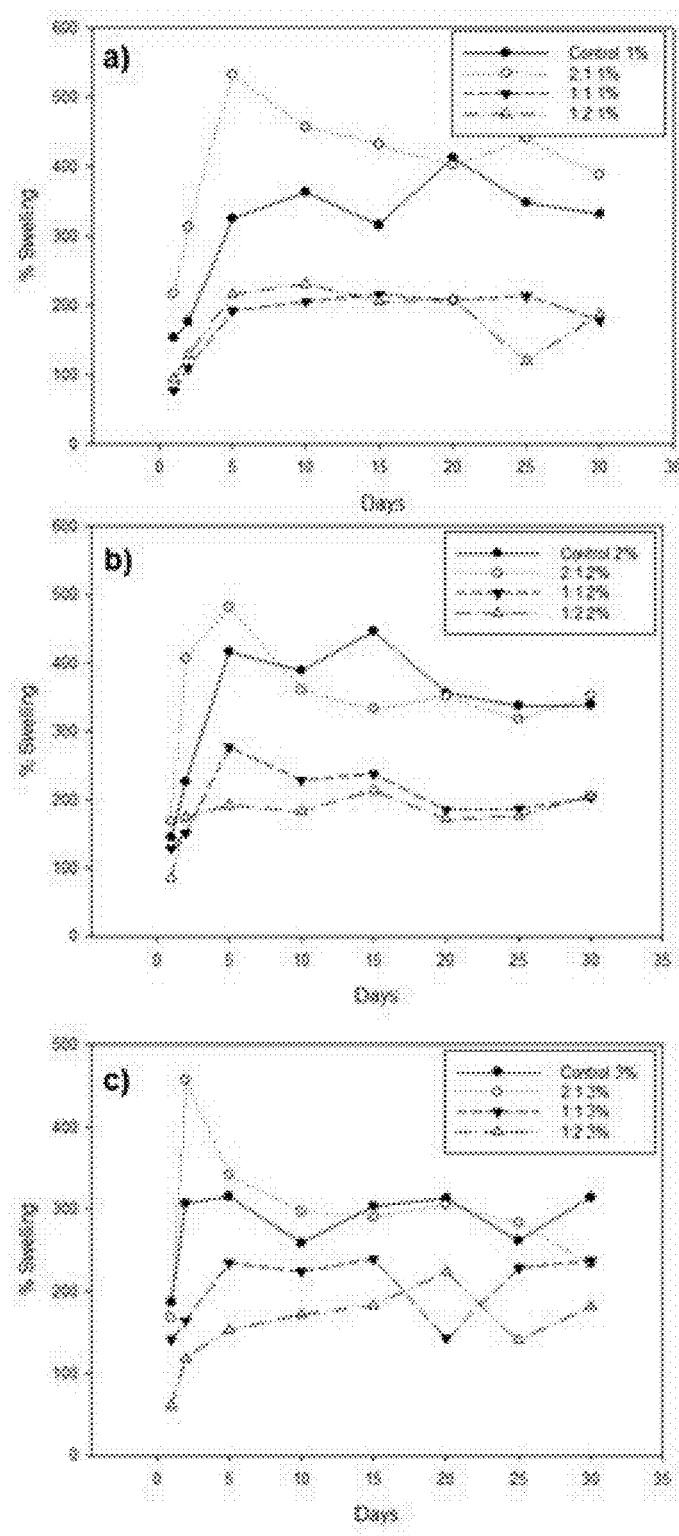
FIGURE 3 (a) – (c)

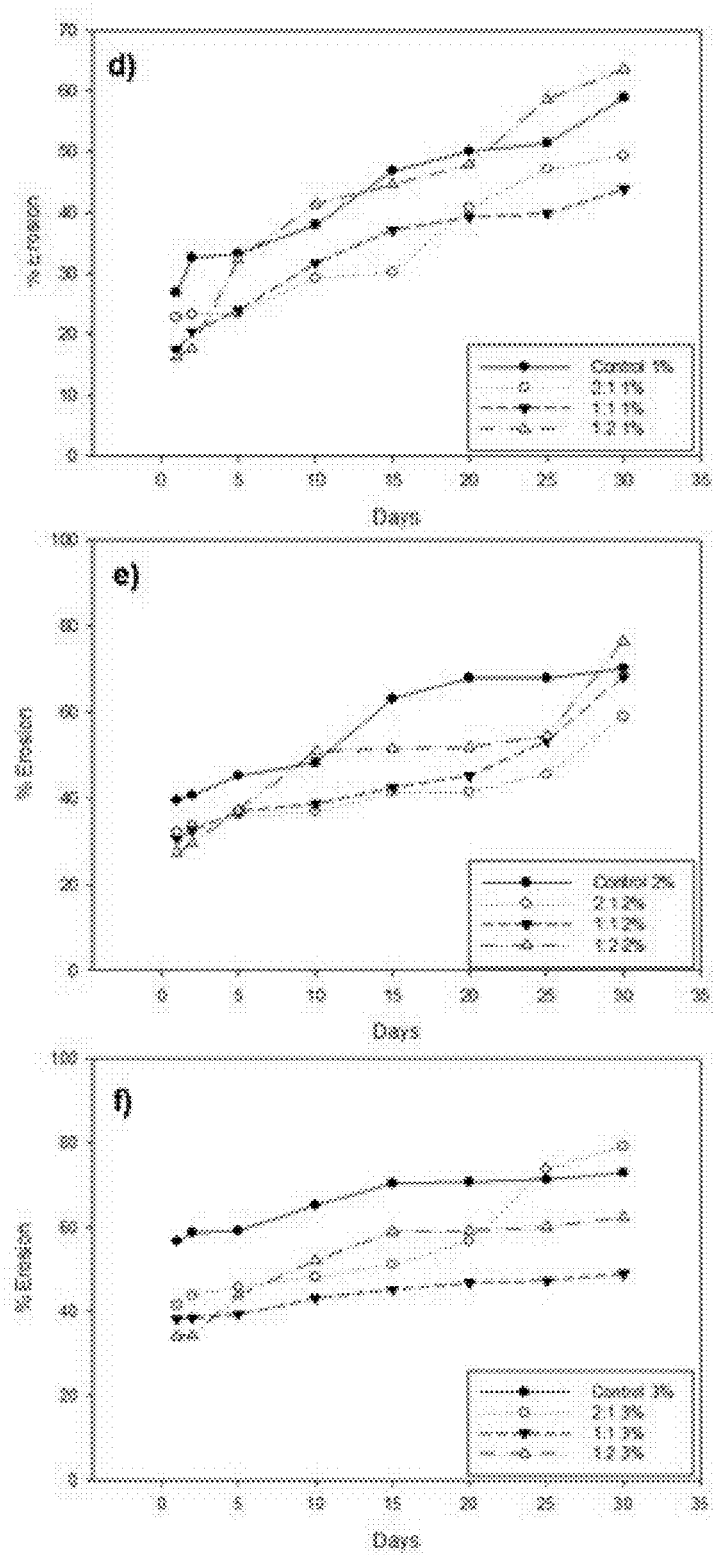
FIGURE 3 (d) – (f)

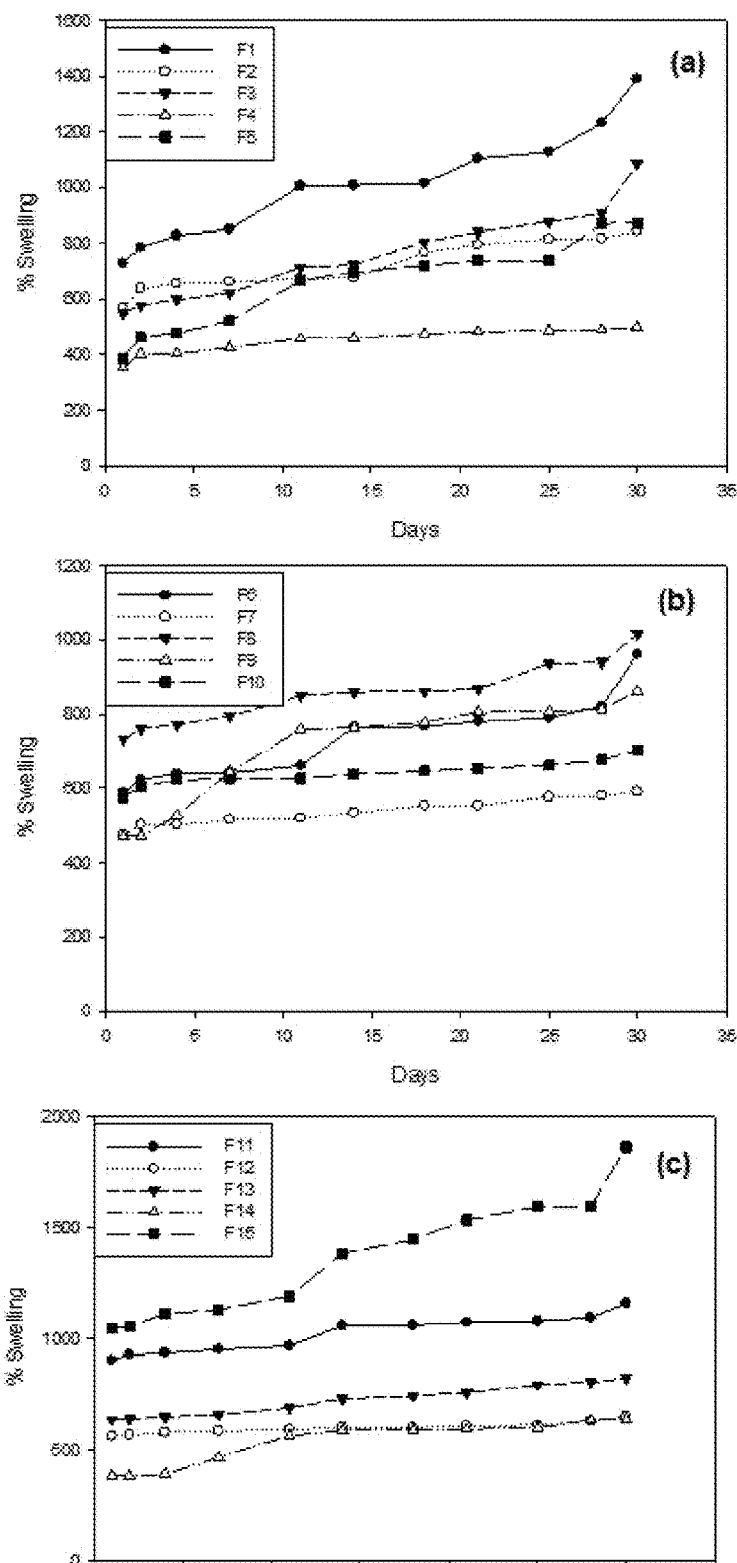
FIGURE 4 (a) – (c)

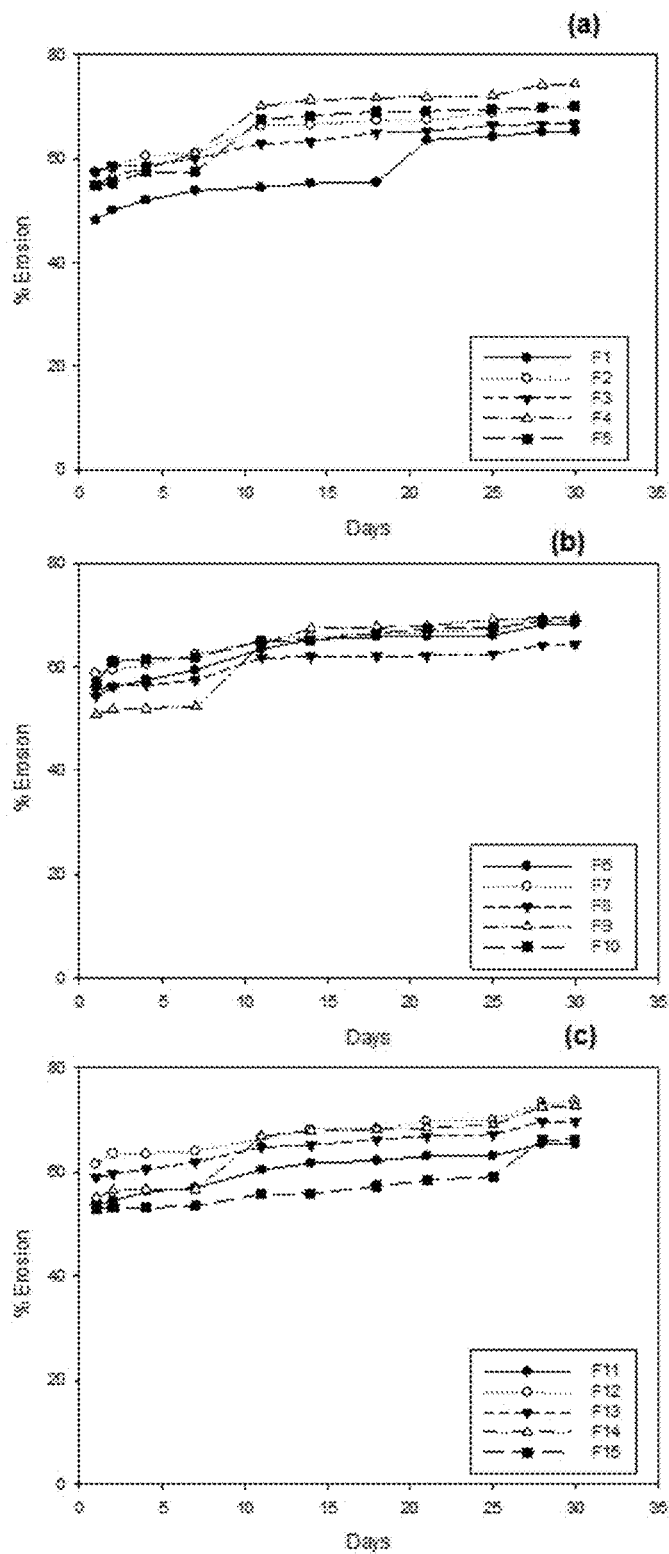
FIGURE 5 (a) – (c)

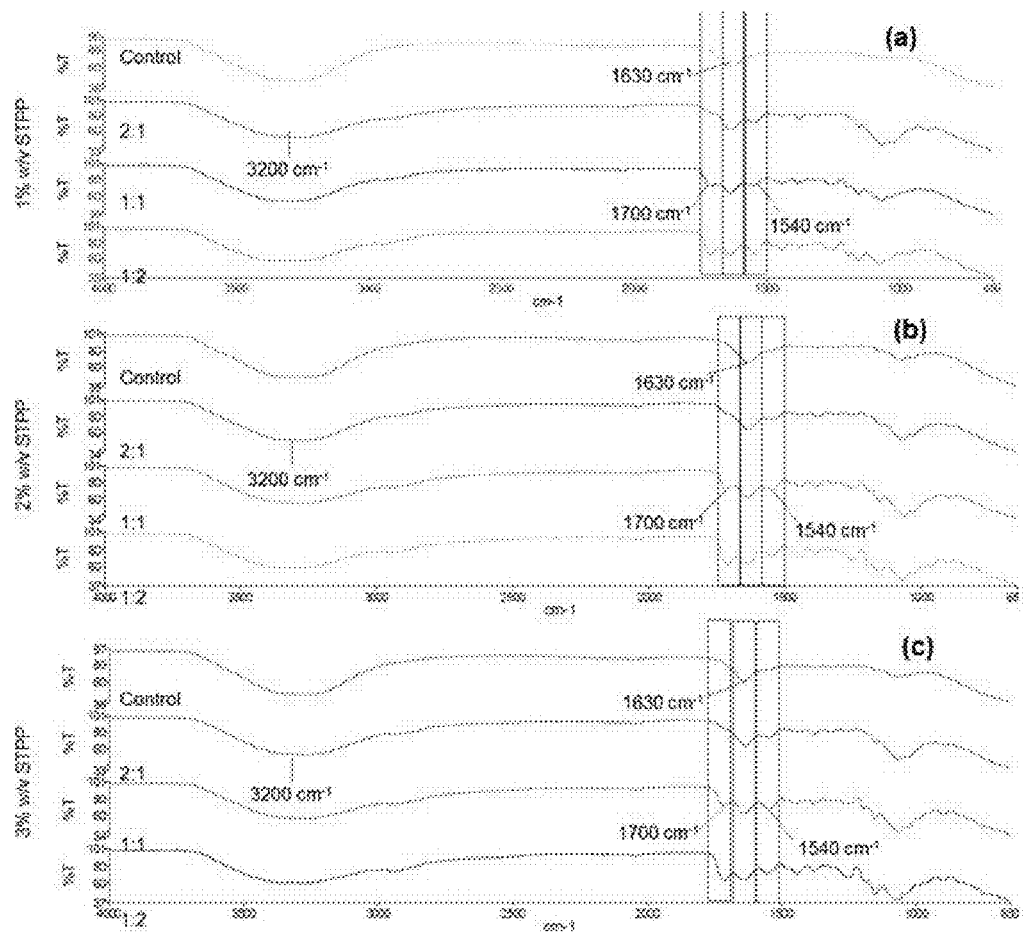
FIGURE 6 (a) – (c)

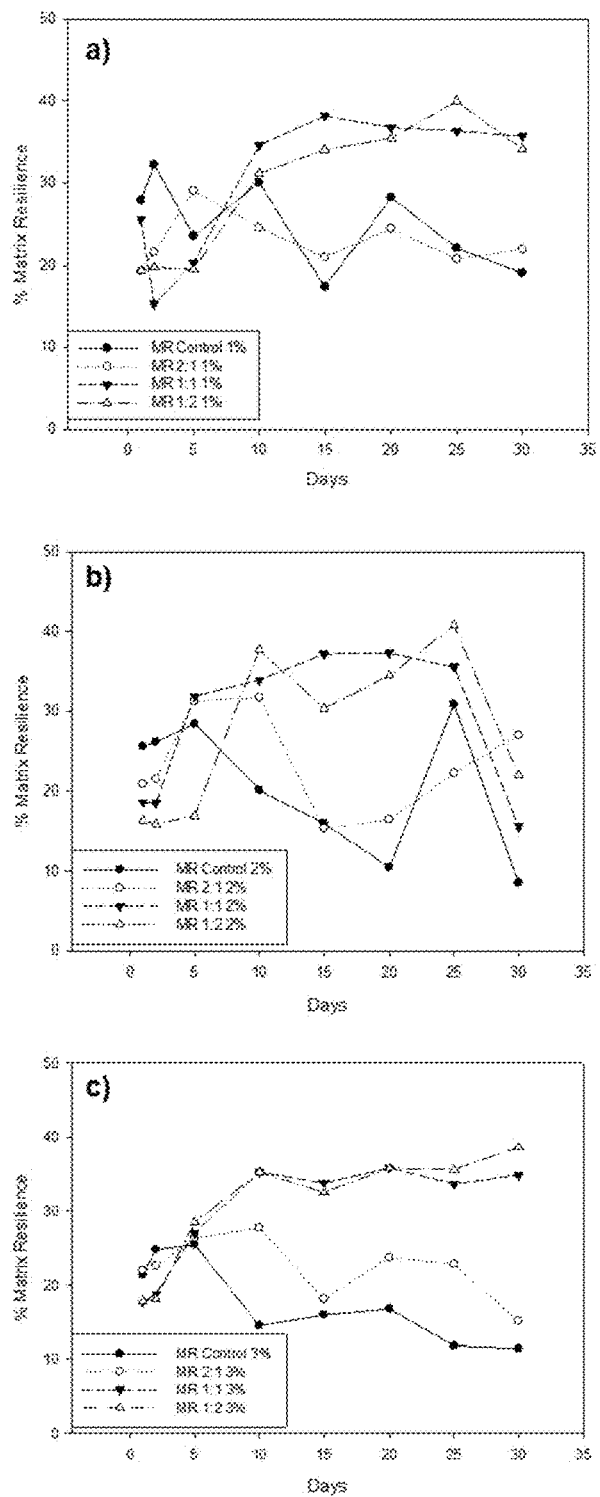
FIGURE 8 (a) – (c)

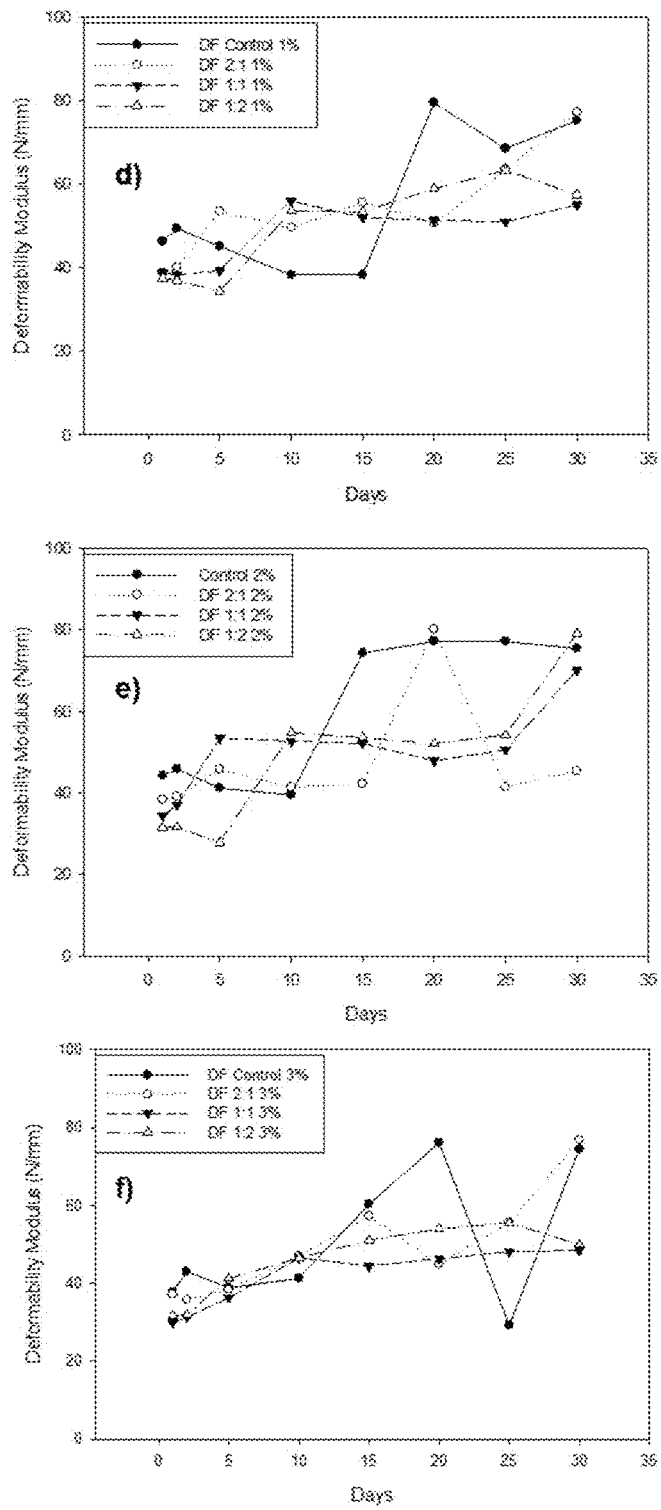
FIGURE 8 (d) – (f)

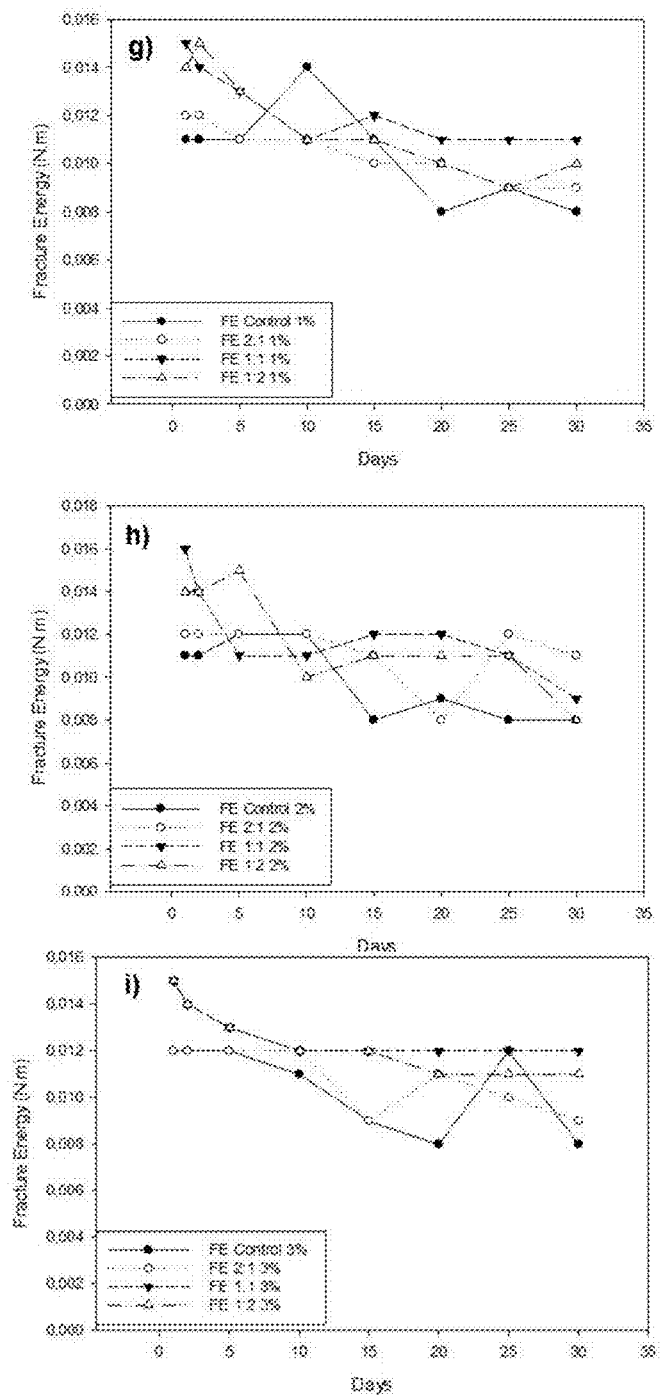
FIGURE 8 (g) – (i)

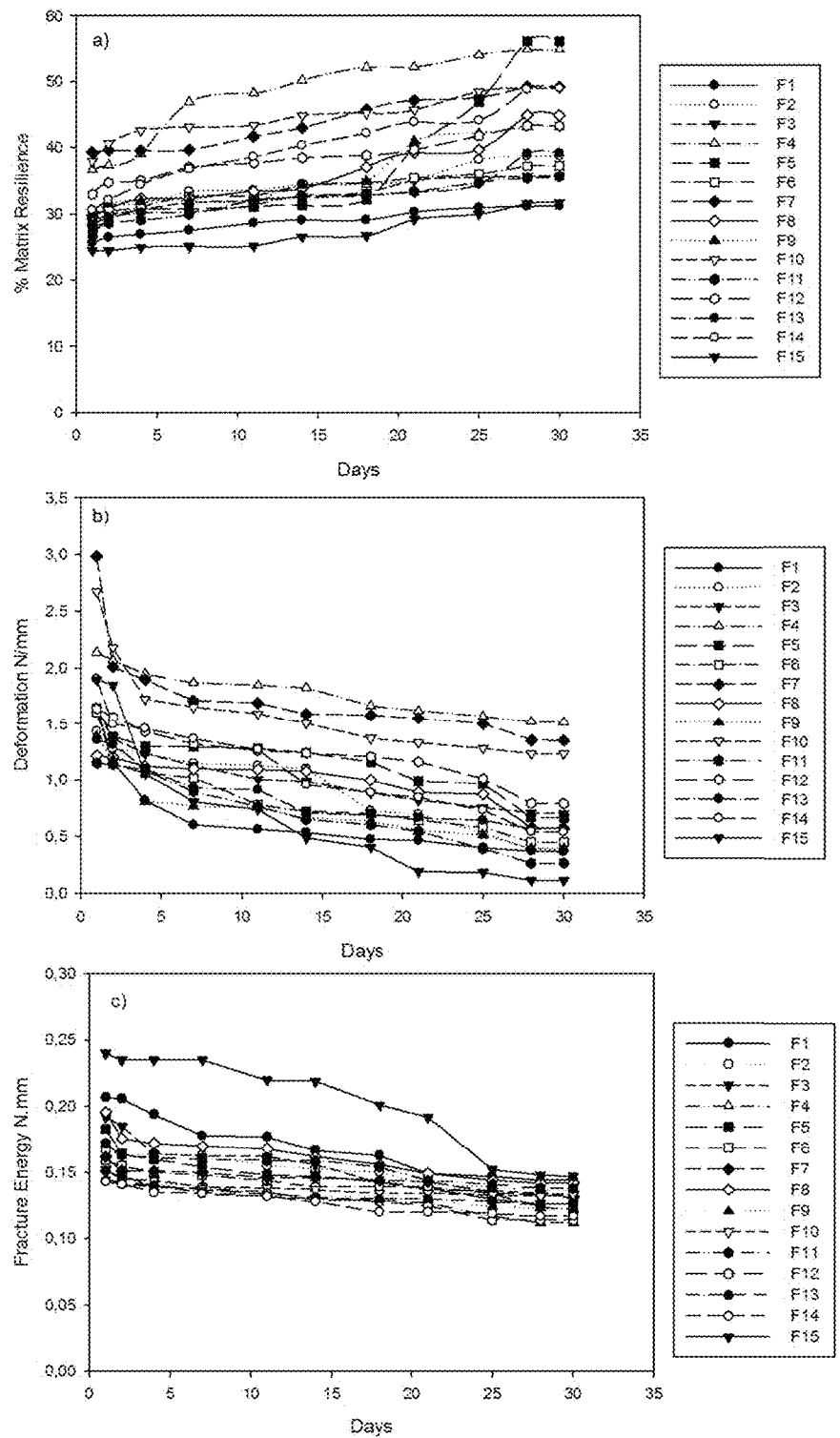
FIGURE 9 (a) – (c)

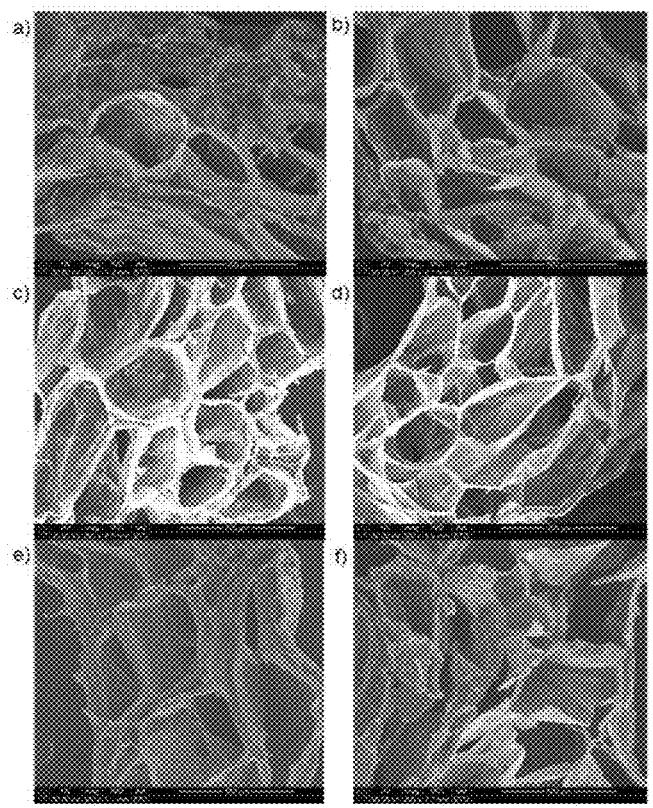
FIGURE 11 (a) – (f)
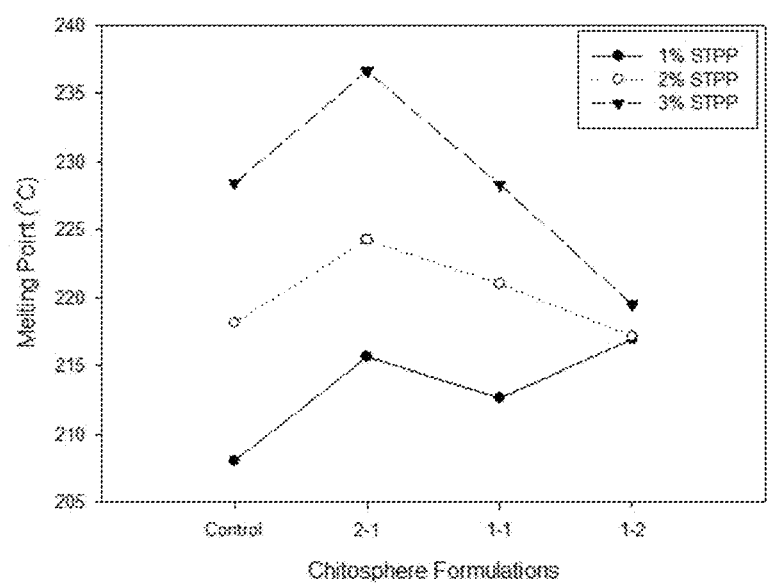
FIGURE 12

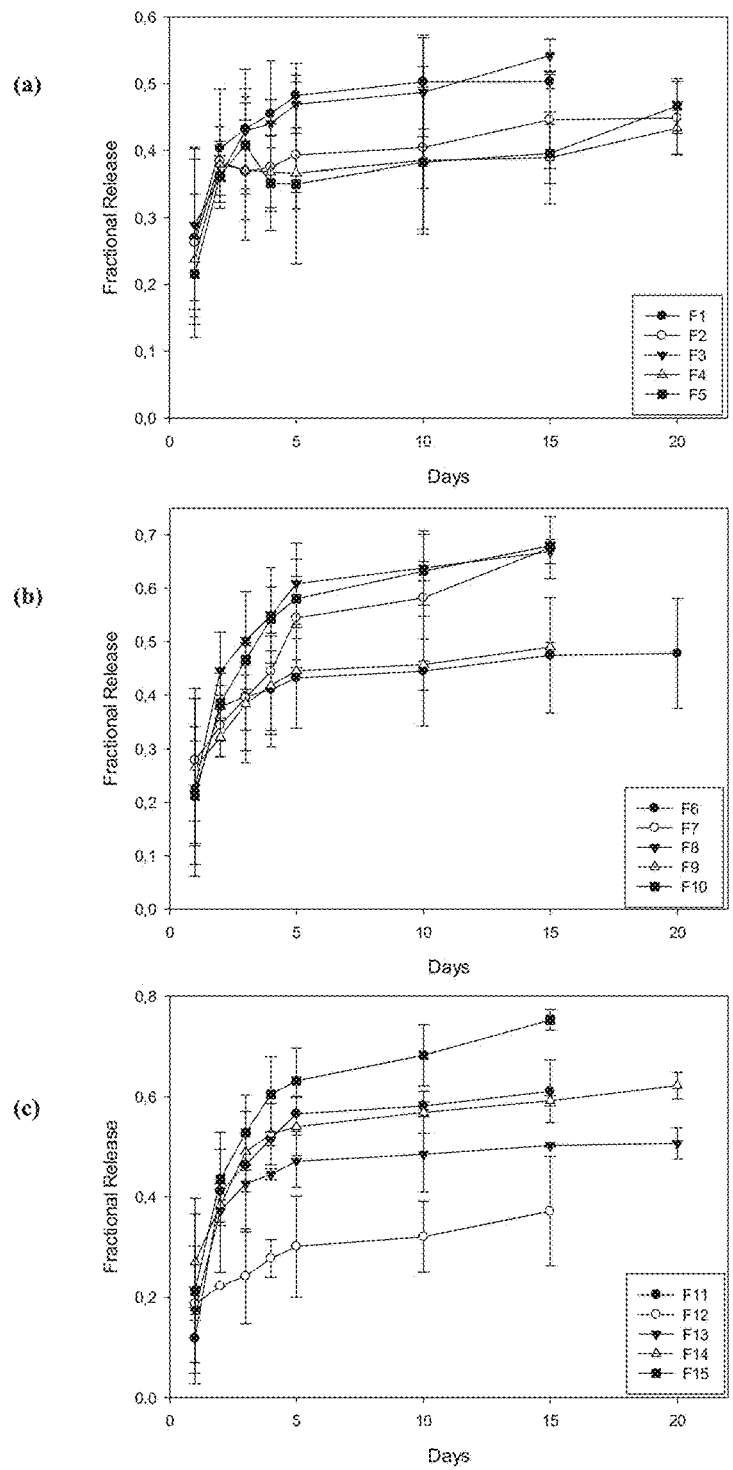
FIGURE 16 (a) – (c)

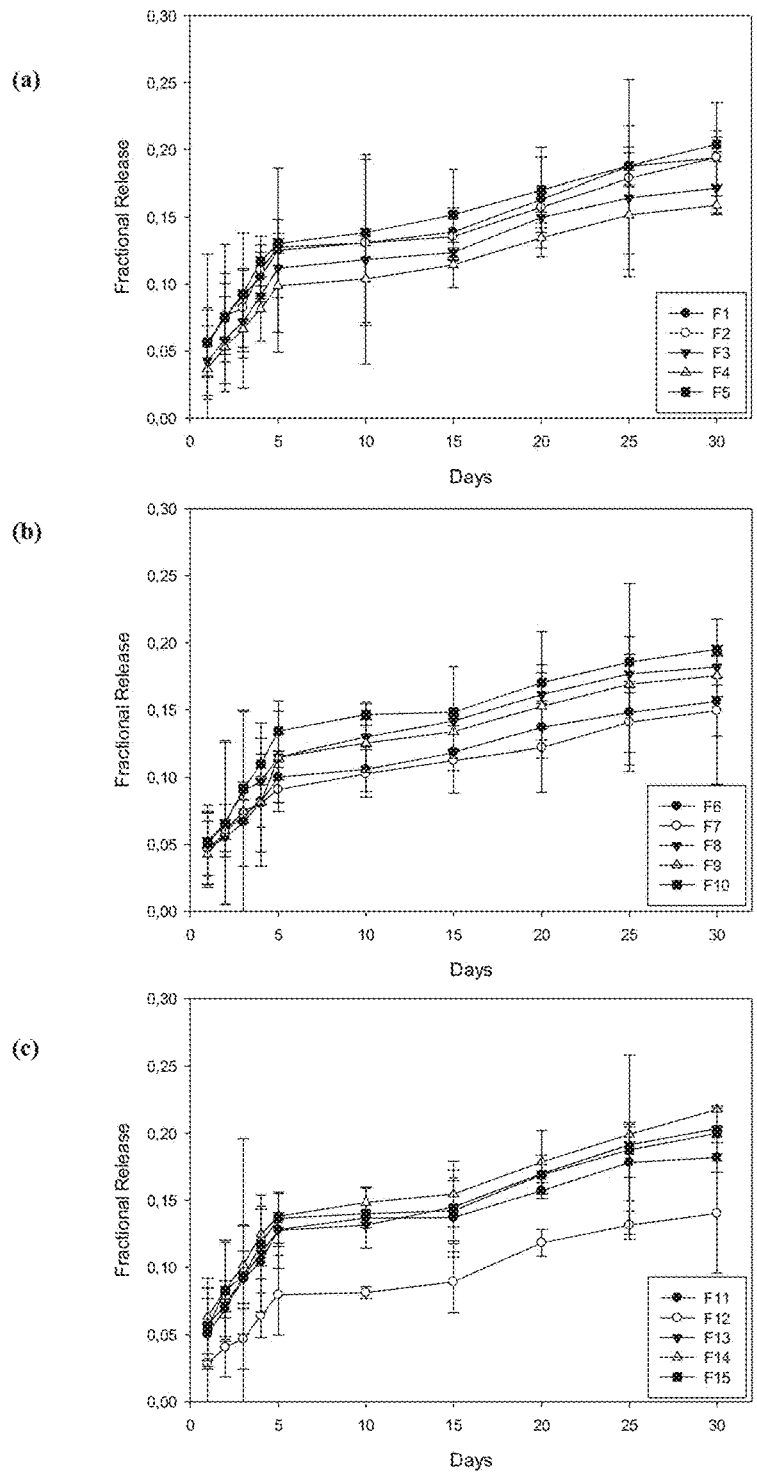
FIGURE 17 (a) – (c)

BIODEGRADABLE IMPLANT

CROSS-REFERENCE TO RELATED APPLICATIONS

This application is a National Stage Application of International Patent Application No. PCT/IB2016/055301, filed Sep. 5, 2016, which claims the benefit of, and priority to, South African Patent Application No. 2015/06544, filed Sep. 4, 2015, the contents of these applications being incorporated entirely herein by reference.

FIELD OF THE INVENTION

This invention relates to biodegradable implants, particularly to biodegradable implants comprising a hydrogel carrier matrix having dispersed therein a multitude of particles, wherein each of the multitude of particles and/or the hydrogel carrier matrix includes an active pharmaceutical ingredient (API) for the treatment of transected peripheral nerve injuries. Each of the multitude of particles and/or the hydrogel carrier matrix includes pristine polymer particles.

BACKGROUND TO THE INVENTION

Transected peripheral nerve injuries from traumatic accidents are known to cause long-term physical disability and neuropathic pain at the injury site. The gold standard of peripheral nerve repair remains the nerve autograft however drawbacks involving multiple surgery sites, lack of donor tissue availability and resulting co-morbidities have reduced its frequent use in the clinical setting. As an alternative to the nerve autograft, a number of polymeric-constructed implants for nerve repair have been introduced onto the market that have shown efficacy in the regeneration of short-gap nerve injuries. Such implants are sutured to either end of the nerve stumps to serve as a bridging device across the gap defect.

While peripheral nerves possess the inherent ability to regenerate and sprout new axons, this innate capacity is often insufficient for the regrowth of an adequately healthy and functional nerve (Soller et al., 20121 Cobianchi et al., 2013). Studies have shown the importance of neurotrophic factors in enhancing the regeneration potential of injured peripheral nerves particularly in gap defects of 10 mm and larger. Thus, research regarding the design of implants for nerve repair has incorporated various single and multiple neurotrophic factors, either in solution or part of a controlled-release mechanism, for enhancing peripheral nerve regeneration. The daily dose of neurotrophic factor delivered to the injury site of the peripheral nerve is critical in the outcome levels of tissue regeneration and functional recovery achieved (Kemp et al., 2011). Under-dosing would have no prominent effect on peripheral nerve regeneration whereas an overdose may hinder the regenerative potential via down-regulation of the necessary receptors (Conti et al., 2004; Goodman and Gilman, 2008). Therefore, tailoring the release kinetics of neurotrophic factors to achieve optimum levels of nerve regeneration is vital for obtaining improvements in functional recovery.

Furthermore, materials comprising the implant should possess intrinsic aspects of native nerve tissue yet be able to maintain adequate mechanical stability and provide the release of sufficient bioactives (APIs) in a sustained manner for the duration of peripheral nerve regeneration. Further research is required to evaluate the role of delivery systems, release mechanisms and release kinetics on the optimal delivery of neurotrophic factors (NTFs) in the most beneficial doses for enhanced axonal sprouting. Such factors must be tailored to deliver NTF doses that correspond to the regeneration rate of the injured tissues. Furthermore, understanding the mechanisms behind the phenomenon of initial burst release and factors controlling the characteristics of sustained release profiles will allow researchers to gain a deeper insight and knowledge on modification techniques to regulate the delivery of incorporated bioactives.

Known biodegradable implants typically comprise a carrier matrix (also called a scaffold) that is impregnated with active pharmaceutical ingredient (API). Once implanted into an animal or human body, the implant comes into contact with bodily fluid causing swelling whilst concomitantly allowing the API to migrate via dissolution processes out of the carrier matrix (scaffold) to a target site to treat a disease, condition and/or injury. Often the swelling of the carrier matrix (scaffold) places unwanted pressure on surrounding tissue and/or slows API release to the target site. Swelling may even result in displacement of the implant preventing the API from reaching its target site.

Accordingly, there is a need for biodegradable implants that at least ameliorate one of the disadvantages known in the prior art and/or described above.

SUMMARY OF THE INVENTION

Broadly, and in accordance with this invention there is provided for a biodegradable implant comprising a hydrogel carrier matrix having dispersed therein a multitude of spheroidal particles, each spheroidal particle including a first polysaccharide and a pristine polymer particle.

The pristine polymer particle may be selected from the group comprising polymethylmethacrylate polymers and derivatives thereof, preferably poly(methacrylic-co-methyl methacrylate) (PMMA) and derivatives thereof, further preferably PMMA nanoparticles.

The hydrogel carrier matrix may comprise a second polysaccharide. Typically, the first polysaccharide is cationic and the second polysaccharide is anionic.

In accordance with a first aspect of this invention there is provided a biodegradable implant comprising a hydrogel carrier matrix having dispersed therein a multitude of spheroidal particles, each spheroidal particle including cross-linked cationic chitosan (CHT) having dispersed therein anionic poly(methacrylic-co-methyl methacrylate) (PMMA) nanoparticles.

The PMMA nanoparticles may be in the form of pristine PMMA nanoparticles.

Each of the spheroidal particles may further include, dispersed therein, a first active pharmaceutical ingredient (API).

The spheroidal particles may each include an outer shell comprising a chitosan (CHT) poly(methacrylic-co-methyl methacrylate) (PMMA) polyelectrolyte complex (CHT-PMMA-PEC) and an inner core comprising crosslinked chitosan having dispersed therein PMMA nanoparticles.

The outer shell of CHT-PMMA-PEC may be formed in situ when the spheroidal particles contact an aqueous medium, therein providing for constant release of the first API therefrom. The aqueous medium is typically inside a human or animal body where the biodegradable implant is implanted/inserted into when in use. The implantation/insertion is typically via surgical means. Surgical implantation may include the use of sutures of fibrin or a biocompatible cyanoacrylate sealant or adhesive.

The outer shell of CHT-PMMA-PEC and/or the inner core may further include pores. The pores may be formed in situ when the outer shell and/or the inner core contacts an aqueous medium of pH between about 5 and about 9, preferably a pH greater than about 7, further preferably a pH of about 7.4, therein dissolving the PMMA to provide pores. The pores may provide for facilitating dissolution of the first API out of the spheroidal particle.

The hydrogel carrier matrix may comprise at least one anionic polysaccharide. Typically, the at least one anionic polysaccharide includes two anionic polysaccharide to form a blend. The two anionic polysaccharides may include xanthan gum and gellan gum forming a xanthan gum-gellan gum blend.

The hydrogel carrier matrix may further include a cross-linking agent. Typically, the blend may further include a crosslinking agent. The xanthan gum-gellan gum blend may be crosslinked to form a crosslinked xanthan gum-gellan gum matrix.

The hydrogel carrier matrix may further include poly (methacrylic-co-methyl methacrylate) (PMMA). The PMMA may be in the form of pristine PMMA particles. In a preferred embodiment of the invention, the pristine PMMA particles are pristine PMMA nanoparticles. The PMMA may intercalate between the crosslinked xanthan gum-gellan gum matrix and/or be dispersed therebetween to form an interpenetrating polymer network. Typically, the PMMA nanoparticles are dispersed throughout the hydrogel carrier matrix.

The hydrogel carrier matrix may further include a second active pharmaceutical ingredient (API).

The first API (dispersed through the spheroidal particles) and the second API (dispersed through the hydrogel carrier matrix) may be the same API, or alternatively, different APIs. The first and/or second API may comprise small molecular weight drugs and/or macromolecular proteins and/or peptides. The macromolecular protein or peptide may be selected from the class of neurotrophic and neurotropic factors including, but not limited to, nerve growth factor, glial-cell derived neurotrophic factor or brain-derived neurotrophic factor. The first and/or second API may also comprise non-steroidal anti-inflammatory agents, preferably diclofenac, ketoprofen, ibuprofen and indomethacin; opioid analgesics, preferably morphine; and glucocorticoids, preferably hydrocortisone, dexamethasone, betamethasone, methylprednisolone and triamcinolone.

The hydrogel carrier matrix may further include pores. The pores may be formed in situ when the hydrogel carrier matrix contacts an aqueous medium of pH between about 5 and about 9, preferably a pH greater than about 7, further preferably a pH of about 7.4, therein dissolving PMMA to provide pores, which pores provide for dissolution of the second API out of the hydrogel matrix.

The hydrogel carrier matrix may be shaped and/or dimensioned to provide an elongate cylinder or an elongate conduit.

The crosslinking agent may be any one or more selected from the group comprising, but not limited to: calcium chloride or any salts of calcium, magnesium, zinc, barium, aluminium and potassium.

The hydrogel carrier matrix may further include at least one plasticising agent selected from the group comprising, but not limited to: propylene glycol, glycerol, polyethylene glycol and triethyl citrate.

Typically, the hydrogel carrier matrix may comprise a polysaccharide blend consisting of gellan gum and xanthan gum each at a concentration 1 w/v, a plasticising agent, preferably propylene glycol at a concentration of 5 w/v, an ionic crosslinking agent (crosslinker), preferably calcium chloride at concentrations of 0.05-0.1 w/v and pristine polymer particles, preferably PMMA nanoparticles, at concentrations of 25-75 w/v. The hydrogel carrier matrix may be produced as a placebo, alternatively, it may include the second API.

In accordance with a second aspect of this invention there is provided for use of the biodegradable implant described in the first aspect in the manufacture of a medicament for treating peripheral nerve injuries or neuropathy.

In accordance a third aspect of this invention there is provided a biodegradable implant described in the first aspect for use in the treatment of peripheral nerve injuries or neuropathy.

In accordance with a fourth aspect of this invention there is provided a method of treating peripheral nerve injuries including the step of implanting a biodegradable implant described in the first aspect at a site of peripheral nerve injury in a human or animal body.

The peripheral nerve injuries may include transection gap-defect nerve injuries.

There is further provided for a biodegradable implant and/or use thereof and/or method of treating peripheral nerve injuries, substantially as herein described, illustrated and/or exemplified with reference to any one of the accompanying diagrammatic drawings and/or examples.

BRIEF DESCRIPTION OF THE DRAWINGS

Embodiments of the invention will be described below by way of example only and with reference to the accompanying drawings in which:

FIG. 3 shows % swelling (a-c) and % erosion (d-f) of chitosphere formulations over 30 days;

FIGS. 4 (a) to (c) shows % swelling of the gellan-xanthan hydrogel carrier matrix Formulations 1 to 15 over 30 days;

FIGS. 5 (a) to (c) shows % Erosion of the gellan-xanthan hydrogel carrier matrix Formulations 1 to 15 over 30 days;

FIGS. 6 (a) to (c) shows spectra showing the FTIR analysis of the various chitospheres formulations, after 24 hours of hydration in PBS pH 7.4, categorised according to the % w/v strength of sodium tripolyphosphate used;

FIG. 8 shows textural analysis profiles featuring the % MR (a-c), DF (d-f) and FE (g-i) of the respective chitospheres formulations;

FIG. 9 shows textural profiles gellan-xanthan hydrogel carrier matrix Formulations 1 to 15: a) Matrix resilience, b) Deformation, c) Fracture energy;

FIG. 11 shows SEM cross-section imaging, at 200× magnification, of selected profiles gellan-xanthan hydrogel carrier matrix Formulations for visualisation of morphological properties: 60:40 a) F9 and b) F11; 70:30 c) F5 and d) F15; 80:20 e) F14 and f) F8;

FIG. 12 shows a profile depicting the influence of pristine PMMA particles concentration on the melting point of the chitospheres;

FIG. 16 (a) to (c) shows API/drug release profiles of BSA from gellan-xanthan blend hydrogel carrier matrix Formulations 1 to 15; and FIG. 17 (a) to (c) shows API/drug release profiles of diclofenac sodium from gellan-xanthan hydrogel carrier matrix Formulations 1 to 15.

DESCRIPTION OF PREFERRED EMBODIMENTS OF THE INVENTION

Figure 1:
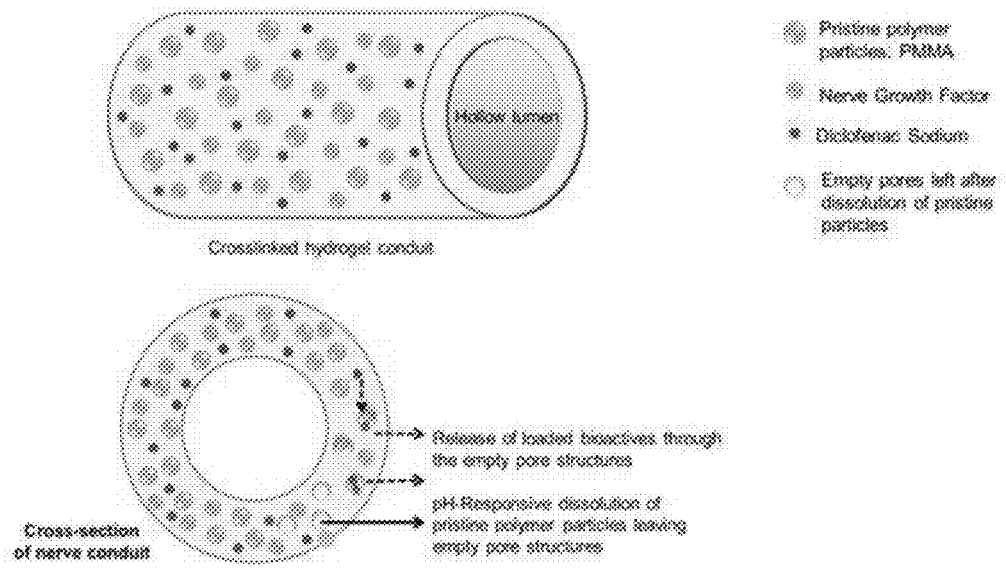
FIG. 1 shows an example design of a gellan-xanthan blend crosslinked hydrogel carrier matrix in the form of a conduit with pristine polymer particle intercalation/dispersion, an elongate cylindrical design is also envisaged but not shown.

The teachings of the Summary are repeated herein by reference thereto, and may not be fully repeated to avoid repetition. Non-limiting, preferred embodiments of the invention are described herein below.

In general terms, this invention relates to biodegradable implants comprising a hydrogel carrier matrix (scaffold) having dispersed therein a multitude of particles, wherein each of the multitude of particles and/or the hydrogel carrier matrix may include an active pharmaceutical ingredient (API) for the treatment of transected peripheral nerve injuries.

Each of the multitude of particles and/or the hydrogel carrier matrix includes pristine polymer particles, preferably the pristine polymer particles may be polymethylmethacrylate polymers and derivatives thereof, preferably poly(methacrylic-co-methyl methacrylate) (PMMA), further preferably PMMA nanoparticles.

The particles are formed as spheres. Each spheroidal particle may include a cationic polysaccharide and PMMA, typically the cationic polysaccharide is chitosan (CHT). Typically, each spheroidal particle includes crosslinked cationic chitosan (CHT) having dispersed therein anionic poly (methacrylic-co-methyl methacrylate) (PMMA) nanoparticles. Each of the spheroidal particles may further include, dispersed therein, a first active pharmaceutical ingredient (API). The spheroidal particles may each include an outer shell comprising a chitosan (CHT) poly(methacrylic-co-methyl methacrylate) (PMMA) polyelectrolyte complex (CHT-PMMA-PEC) and an inner core comprising crosslinked chitosan having dispersed therein PMMA nanoparticles. The outer shell of CHT-PMMA-PEC may be formed in situ when the spheroidal particles contact an aqueous medium, therein providing for constant release of the first API therefrom. The aqueous medium is typically inside a human or animal body where the biodegradable implant is implanted/inserted into when in use. The implantation/insertion is typically via surgical means. Surgical implantation may include the use of sutures of fibrin or a biocompatible cyanoacrylate sealant or adhesive.

The outer shell of CHT-PMMA-PEC and/or the inner core may further include pores. The pores may be formed in situ when the outer shell and/or the inner core contacts an aqueous medium of pH between about 5 and about 9, preferably a pH greater than about 7, further preferably a pH of about 7.4, therein dissolving the PMMA to provide pores. The pores may provide for facilitating dissolution of the first API out of the spheroidal particle.

The hydrogel carrier matrix may comprise at least one anionic polysaccharide. Typically, the at least one anionic polysaccharide includes two anionic polysaccharide to form a blend. The two anionic polysaccharides may include xanthan gum and gellan gum forming a xanthan gum-gellan gum blend.

The hydrogel matrix may further include a crosslinking agent. Typically, the blend may further include a crosslinking agent. The xanthan gum-gellan gum blend may be crosslinked to form a crosslinked xanthan gum-gellan gum matrix.

The hydrogel carrier matrix may further include poly (methacrylic-co-methyl methacrylate) (PMMA). The PMMA may be in the form of pristine PMMA particles. In a preferred embodiment of the invention, the pristine PMMA particles are pristine PMMA nanoparticles. The PMMA may intercalate between the crosslinked xanthan gum-gellan gum matrix and/or be dispersed therebetween to form an interpenetrating polymer network. Typically, the PMMA nanoparticles dispersed throughout the hydrogel carrier matrix.

The hydrogel carrier matrix may further include a second active pharmaceutical ingredient (API). The first API (dispersed through the spheroidal particles) and the second API (dispersed through the hydrogel carrier matrix) may be the same API, or alternatively, different APIs. The first and/or second API may comprise small molecular weight drugs and/or macromolecular proteins and peptides. The macromolecular protein or peptide may be selected from the class of neurotrophic and neurotropic factors including, but not limited to, nerve growth factor, glial-cell derived neurotrophic factor or brain-derived neurotrophic factor. The first and/or second API may also comprise non-steroidal anti-inflammatory agents, preferably diclofenac, ketoprofen, ibuprofen and indomethacin; opioid analgesics, preferably morphine; and glucocorticoids, preferably hydrocortisone, dexamethasone, betamethasone, methylprednisolone and triamcinolone.

The hydrogel matrix may further include pores. The pores may be formed in situ when the hydrogel carrier matrix contacts an aqueous medium of pH between about 5 and about 9, preferably a pH greater than about 7, further preferably a pH of about 7.4, therein dissolving PMMA to provide pores, which pores provide for dissolution of the second API out of the hydrogel matrix.

The hydrogel carrier matrix may be shaped and/or dimensioned to provide an elongate cylinder or an elongate conduit. The particular shape and/or dimension may vary and will depend on the shape and/or dimension of corresponding moulds.

The crosslinking agent may be any one or more selected from the group comprising, but not limited to: calcium chloride or any salts of calcium, magnesium, zinc, barium, aluminium and potassium.

The hydrogel carrier matrix may further include at least one plasticising agent selected from the group comprising, but not limited to: propylene glycol, glycerol, polyethylene glycol and triethyl citrate.

Typically, the hydrogel carrier matrix may comprise a polysaccharide blend consisting of gellan gum and xanthan gum each at a concentration 1 w/v, a plasticising agent, preferably propylene glycol at a concentration of 5 w/v, an ionic crosslinking agent (crosslinker), preferably calcium chloride at concentrations of 0.05-0.1 w/v and pristine polymer particles, preferably PMMA nanoparticles, at concentrations of 25-75 w/v. The hydrogel carrier matrix may be produced as a placebo, alternatively, it may include the second API.

The present invention entails the use of natural hydrophilic polysaccharide blends (particularly exemplified herein as gellan gum and xanthan gum blend) for the formation of crosslinked hydrogel carrier matrices (scaffolds) via an ionic physical crosslinking mechanism. The concurrent modulated API/drug release of two bioactive agents is provided via the intercalation (dispersion) of pristine polymer particles (particularly exemplified herein as pristine poly(methacrylic-co-methyl methacrylate) (PMMA)) within the hydrogel carrier matrix. It is postulated that the pH-responsive dissolution of the intercalated (dispersed) particles at pH 7.4 results in the formation of pores. The ultimate release of bioactives/APIs/drug is further controlled by the rate of water-uptake, swelling, the time-dependent dissolution of the pristine polymer particles and final disentanglement and erosion of the polymer chains.

Swellability of the biodegradable implant is reduced and API/drug release is prolonged. These physico-chemical properties provides for advantages in the field of biodegradable implants. Particularly, in the field of biodegradable implants for peripheral nerve repair, these are noteworthy advantages since limited swelling prevents excess pressure exerted onto adjacent tissue and/or dislodgment of the implant from a site of treatment. Furthermore, prolonged drug release allows for an implant to be inserted and to provide for API release at the treatment site for a long period of time.

FIG. 1 depicts the design of the hydrogel carrier matrix (scaffold) comprising an anionic crosslinked polysaccharide blend of gellan gum and xanthan gum and the pristine poly(methacrylic-co-methyl methacrylate) particles (PMMA) intercalated (dispersed) therein. FIG. 1 shows the hydrogel carrier matrix (scaffold) formed as a conduit. It is to be understood that the shape and/or dimension will depend on the corresponding shape of a mould used in its manufacture. Elongate cylindrical hydrogel carrier matrices (scaffolds) are also envisioned.

Figure 2:
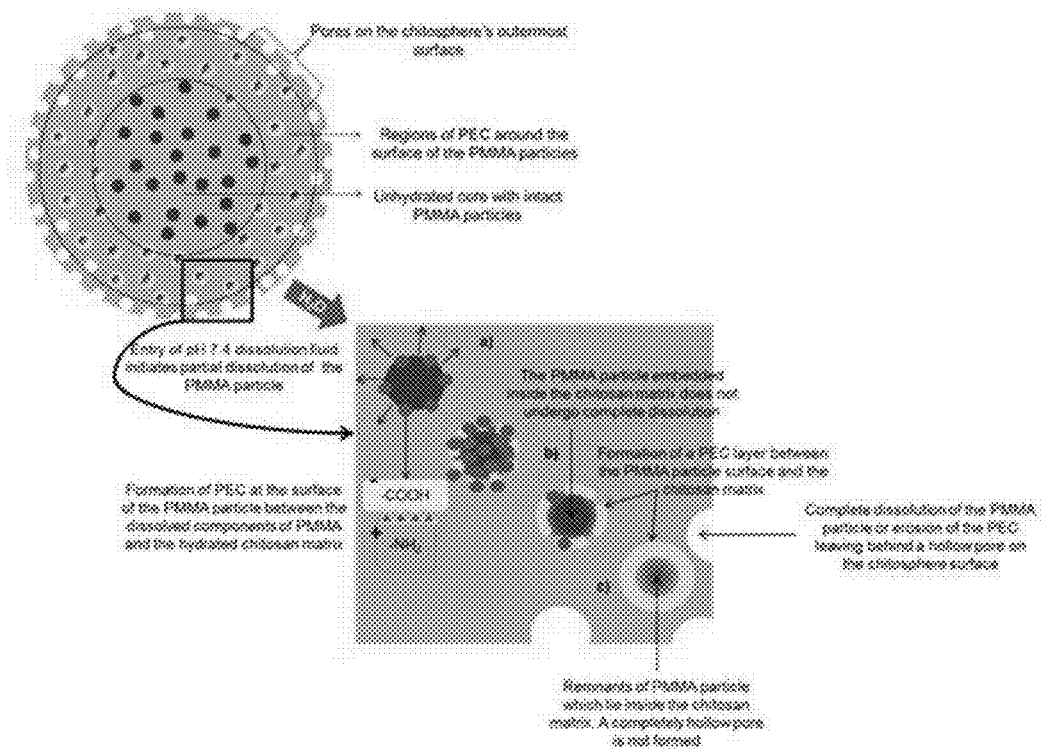
FIG. 2 shows a schematic illustration of a mechanism of polyelectrolyte complexation between anionic poly(methacrylic-co-methyl methacrylate) (PMMA) particles and cationic chitosan and pore formation upon the pH-responsive dissolution of PMMA in the chitospheres.

FIG. 2 illustrates the mechanism of polyelectrolyte complexation and pore formation upon the pH-responsive dissolution of the intercalated (dispersed) pristine PMMA particles of the spheroidal particles (chitospheres). Incorporation of the anionic PMMA particles into a cationic matrix base, chitosan, produces the formation of hollow core microenvironments (pores) including polyelectrolyte complexation (when in use) whereas intercalation within the anionic gellan/xanthan gum blend contributes to the possible formation of both hollow core and gelled microenvironment structures (when in use) depending on the ratio of the constituent polymers. Hollow core microenvironment structures may result in increased rates of API/drug release whereas gelled core microenvironments slow the rate of drug release by hindering the movement of drug molecules through the gel-filled pore.

Polysaccharides constitute a class of biopolymers comprising simple sugar monomers linked together via O-glycosidic bonds that may be arranged to form various linear and branched polymers. The composition, position, chain shape and molecular weight of the repeating monomers determine the surface properties and solubility and gelling characteristics of the polymer. Natural polysaccharide materials are often hydrophilic and can be obtained from several sources: animals, plants, bacterial and fungal. Their non-toxic, biocompatible, haemocompatible and biodegradable properties have popularised its use in scaffold-based materials for tissue engineering applications and drug delivery systems (Malafaya et al., 2007).

Chitosan obtained from the chitin copolymers of glucosamine and N-acetyl-D-glucosamine is a cationic polymer widely used in the fabrication of oral drug delivery technologies, tissue engineering and wound healing applications due to its bioadhesive properties in the swollen state (Malafaya et al., 2007). Moreover, chitosan has been modified with various synthetic or natural polymer gums, opposite in ionic charge, for polyelectrolyte complexation for sustained drug release rates.

Gellan gum is an anionic bacterial exopolysaccharide widely used in the food industry as an additive for gelling and viscosity enhancer. It consists of repeating tetrasaccharide unit of two glucose, one glucuronic acid and one rhamnose molecule. Gellan gum solutions readily undergo ionotropic gelation to form physically crosslinked gels, hence its wide studies relating to the manufacture of in situ gelling ophthalmic preparations for enhanced drug delivery and bioavailability (Coutinho et al., 2010).

Xanthan gum is a high molecular weight anionic bacterial heteropolysaccharide. Being water soluble, it is frequently used as a viscosity-modifying agent in the food industry. Due to its hydrophilic, inert and biocompatible nature, it has further been proved to retard drug release providing time dependent release kinetics (Singh et al., 2011). However, its weak gelling properties following physical crosslinking is unsuitable for use in the development of long-term tissue implants and scaffolds.

Poly(methacrylic-co-methyl methacrylate) (PMMA) is an anionic synthetic hydrophobic acrylate copolymer comprising varying ratios of methacrylic acid and methyl methacrylate. Such polymers, being able to disintegrate upon wetting, different pH ranges are used for the fabrication of oral enteric drug delivery systems for the delivery of acid-labile proteins and for targeted delivery of other pharmaceutical compounds at specific sites of the intestinal tract (Jain et al., 2005; Kachrimanis et al., 1998; Khan et al., 2000) where the polymer comprises the matrix alone or serves as a protective coating (Paharia et al., 2007). Eudragit S100 consisting of poly(methacrylic acid-co-methyl methacrylate) in a 1:2 ratio undergoes dissolution at a pH>7.0. Intercalation (dispersion) of such particles into a gel matrix is shown herein below to result in the in situ formation of pores, via particulate leaching, for controlled delivery of bioactives (APIs/drugs) and improvement of resilience properties.

The above mentioned polysaccharide polymers are crosslinked with ionic multivalent (sodium tripolyphosphate) and divalent (calcium chloride) ions for the induction of physical crosslinking and ionotropic gelation of chitosan and gellan/xanthan gum blends, respectively. Ionic crosslinkers are being frequently used as crosslinking agents as in addition to providing rapid crosslinking action, they are considered to be safer compared to chemical crosslinkers that have the potential to cause physiological toxicity (Mi et al., 1999; Shu and Thu, 2002; Li and Huang, 2012; Shenvi et al., 2014). The ionically crosslinked gellan/xanthan network and its gelation property was further enhanced via a thermal-induced chain conformation resulting in the transition of the coiled network to a helical structured one. Furthermore, the gellan/xanthan gum blend hydrogel carrier matrix (scaffold), crosslinked via ionic and thermal means, results in the formation of a an interpenetrating polymer network thereby providing the entrapment and sustained release of API/drug and/or protein by modification of the network properties. The water-uptake, swelling and subsequent transition change of xanthan gum from a gel-sol state provides for the formation of gelled pores inhibiting the transport rate of drug molecules out of the matrix network. In addition, varying the ratios of gellan and xanthan gum provides for the tuning of mechanical properties regarding the balance between rigidity (strength) and flexibility of implant post hydration. The hydrogel carrier matrix is able to absorb water many-fold its weight for biocompatibility with native tissues. Complex processes involving water-uptake, swelling, polymer chain relaxation and subsequent polymer erosion results in drug release via diffusion as the matrix undergoes changes at the glassy/rubbery interface as water-penetration continues (Singh et al., 2011).

Materials and Methods

Gellan gum (Gelzan™ CM), xanthan gum, chitosan (poly D-glucosamine, deacetylated chitin, medium molecular weight), diclofenac sodium, indomethacin (>99% TLC), bovine serum albumin (BSA), sodium tripolyphosphate (technical grade, 85%) and dialysis tubing cellulose membrane (molecular weight cut-off=14 000 Da) were purchased from Sigma Aldrich, Steinham, Germany. Poly(methacrylic-co-methyl methacrylate) (Eudragit S100) was purchased from Evonik, Midrand, Johannesburg, South Africa and was used without further modifications as the pristine polymer particles. Propylene glycol was purchased from Merck, Darmstadt, Germany and calcium chloride anhydrous was purchased from Rochelle Chemicals, Johannesburg, South Africa. Acetic acid glacial (98.5%) and ethanol (99% absolute) were purchased from AceChem (Johannesburg, Gauteng, South Africa) and LabChem (Edenvale, Gauteng, South Africa) respectively. Milipore water was used for all the preparations.

Synthesis of the Hydrogel Carrier Matrix

The hydrogel carrier matrix (scaffold) comprises anionic polysaccharides and PMMA (poly(methacrylic-co-methyl methacrylate). In a preferred embodiment of the carrier matrix the anionic polysaccharides include gellan gum and xanthan gum. The hydrogel carrier matrix (scaffold) may further include a plasticizer and/or a crosslinker.

Gellan gum and xanthan gum powders of ratios between 20-80% were combined and added to deionised water to form a 1 w/v gel solution. After solubilisation of the gum powders, propylene glycol and calcium chloride were added as the plasticiser and crosslinker in concentrations of 5 w/v and 0.05%-0.1 w/v, respectively.

The resultant gel blend was then heated to 100° C. and maintained at that temperature for 10 minutes. Addition of poly(methacrylic-co-methyl methacrylate) (PMMA) (in the form of pristine PMMA nanoparticles) was introduced into the gel blend, in concentrations of 25-75%, after cooling to 60° C., to form a hydrogel-PMMA particle suspension. The PMMA is intercalated/dispersed within the gel blend.

The hydrogel-PMMA particle suspension was slowly cooled to temperatures between 35-37° C. to allow the incorporation of model API/drug and model protein (diclofenac sodium and bovine serum albumin, respectively) to produce an API/drug and protein loaded hydrogel-PMMA particle suspension.

The API/drug and protein loaded hydrogel-PMMA particle suspension was carefully syringed into prepared cylindrical moulds and allowed to set at room temperature for 20 minutes before being removed and left to air-dry in a fumehood for 24 hours. Consequently, a drug loaded intercalated PMMA gellan-xanthan gum hydrogel carrier matrix is formed. Intercalation between PMMA and gellan-xanthan gum impacts API/drug release profiles and/or dissolution and/or biodegradability profiles of the hydrogel carrier matrix.

A series of hydrogel carrier matrices (scaffolds) were synthesised employing a Box-Behnken design as listed in Table 1. The PMMA in the form of pristine PMMA nanoparticles was commercially bought as Eudragit S100 from Evonik, Midrand, Johannesburg.

TABLE 1

Formulations as per the Box-Behnken design

| Formulation | Gellan gum:Xanthan gum | $CaCl_2$ (% w/v) | PMMA(g/g of polysaccharide dry powder) |
|---|---|---|---|
| 1 | 60:40 | 0.1 | 0.50 |
| 2 | 70:30 | 0.075 | 0.50 |
| 3 | 80:20 | 0.1 | 0.50 |
| 4 | 70:30 | 0.05 | 0.75 |
| 5 | 70:30 | 0.1 | 0.75 |
| 6 | 70:30 | 0.075 | 0.50 |
| 7 | 80:20 | 0.05 | 0.50 |
| 8 | 80:20 | 0.075 | 0.25 |
| 9 | 60:40 | 0.075 | 0.75 |
| 10 | 70:30 | 0.05 | 0.25 |
| 11 | 60:40 | 0.075 | 0.25 |
| 12 | 60:40 | 0.05 | 0.50 |
| 13 | 70:30 | 0.075 | 0.50 |
| 14 | 80:20 | 0.075 | 0.75 |
| 15 | 70:30 | 0.1 | 0.25 |

Synthesis of a Multitude of Spheroidal Particles (Chitospheres)

Spheroidal particles in the form of chitospheres were prepared by a method of ionotropic gelation, adapted from Bodmeier, et al. (1989) and Shu and Thu, (2000), using sodium tripolyphosphate (STPP) as the ionic crosslinking agent. In a certain preferred embodiment of the invention, the multitude of spheroidal particles were dispersed through hydrogel carrier matrices (scaffolds) in so doing producing a hydrogel carrier matrix (scaffold) impregnated with a multitude of spheroidal particles, which spheroidal particles may be preferably API/drug loaded.

A 2% w/v chitosan solution was prepared by dissolving chitosan in 1M acetic acid at room temperature until homogenous. The model API/drug, indomethacin (1% w/v), was dissolved in pure ethanol and added to the chitosan solution. After evaporation of ethanol, poly(methacrylic-co-methyl methacrylate) (PMMA) (in the form of pristine PMMA nanoparticles), was added to the chitosan-indomethacin solutions in the following ratios of chitosan to pristine PMMA particles: 2:1, 1:1 and 1:2. The aforementioned resulted in a homogenous distribution of API/drug throughout the polymer solution.

Multiparticulate spheroidal particles were prepared from a chitosan-indomethacin-PMMA solution. These are termed as the drug loaded chitospheres. The chitosan-indomethacin-PMMA solution was dropped through a 21 gauge hypodermic needle into sodium tripolyphosphate crosslinking solutions of 1%, 2% and 3% w/v to form drug loaded chitospheres. The drug loaded chitospheres were left to cure in the crosslinking solutions for 30 minutes before being separated, washed and collected. The drug loaded chitospheres were washed with 1M acetic acid to remove excess drug and any uncrosslinked chitosan from the surface. The drug loaded chitospheres were then dried at 50° C. for 48 hours and stored in a desiccator before further physicomechanical characterization and drug-release profiling.

As discussed in more detail below the cationic chitosan interacted with the anionic poly(methacrylic-co-methyl methacrylate) PMMA in situ to form a polyelectrolyte (PEC) outer layer (shell) whilst an inner core remained as crosslinked chitosan (CHT) having PMMA dispersed therein.

When the spheroidal particles (chitospheres) were exposed to fluid having a pH between about 5 and 9, preferably a pH of 7 or more, further preferably a pH of 7.4, uncomplexed PMMA particles dissolved further facilitating the formation of a polyelectrolyte complex (PEC), whilst also facilitating pore formation through in the chitosphere. The formed pores provided for dissolution of the API/drug and displacement thereof from chitosphere to a target site external to the chitosphere, whilst the PEC provided for an in situ means of controlled, sustained and prolonged drug release. This controlled, sustained and prolonged drug release is advantageous where drug loaded implants are implanted into a human or animal body. Moreover, the formation of pores by action of the dissolution of the PMMA particles impacts the swellability of the chitosphere so as to limit swelling therein providing less pressure on surrounding tissue since the biodegradable implant has a limited increase in volume.

Multiparticulate spheroidal particles were also prepared from a chitosan-indomethacin solution (without the addition of pristine PMMA particles) to provide Control formulations. This was done to verify the surprising and unexpected properties attributed to the presence of PMMA, the formation of a polyelectrolyte complex (PEC), the porogen nature of the PMMA, and the consequent impact on swellability and drug/API release.

Swelling and Erosion Studies
Spheroidal Particle Chitospheres and Hydrogel Carrier Matrix (Scaffold):

Swelling and erosion studies provide insight into the API/drug and/or protein release mechanism by determining the degree of water-uptake into the matrix network of both the API/drug loaded hydrogel carrier matrix (scaffold) and the API/drug loaded spheroidal particles. Size change of the system induced by swelling is an important factor to consider for biodegradable implants, including its erosion properties, as these characteristics affect the mechanical strength of the implant, the in vivo performance and the amount of pressure exerted onto surrounding tissue when in use.

The data shows the percentage swelling and erosion over a period of time for the different spheroidal particles in the form of the manufactured chitospheres (FIG. 3), and gellan-xanthan gum hydrogel carrier matrices (scaffolds) (FIGS. 4 and 5) containing varying quantities of pristine PMMA particles and crosslinker.

All the polysaccharide polymers under study (chitosan, gellan gum and xanthan gum) are hydrophilic natural materials with great propensity for swelling via their water-absorbing properties. Increase in pristine PMMA particle content reduces the swelling capacity of produced chitospheres and the hydrogel carrier matrices (scaffolds). Predicting the impact of PMMA nanoparticles on the swellability is not possible, and the observed reduction in swelling with increasing PMMA is surprising and unexpected. This reduction in swelling with increased PMMA is advantageous for biodegradable implants since it will limit the risk of dislodgment from a treatment site and/or excess pressure being placed on surrounding tissue when in use.

Further in regard to the chitospheres, an increased concentrations of crosslinker in chitosan exhibited reduction in swelling, including swelling-induced size change. However, in the case of gellan-xanthan hydrogel carrier matrices (scaffolds), swelling was enhanced which further increased the size of the hydrated gel carrier matrices (scaffolds). The intermolecular and intramolecular complexes formed between gellan-xanthan, gellan-gellan and xanthan-xanthan chains upon crosslinking promote enhanced holding of the network thereby increasing the hydrogel's water-holding capacity.

Erosion of the produced chitospheres and the hydrogel carrier matrices (scaffolds) decreases with increased crosslinker concentrations, however, the inclusion of pristine polymer particles (in the form of PMMA nanoparticles) had opposing effects on the erosion properties of the hydrogel carrier matrices (scaffolds). Increasing the pristine polymer particle (PMMA nanoparticle) concentrations slowed the erosion of the crosslinked chitosan matrices. Slowed erosion allows for a longer acting biodegradable implant when in use, which is particularly advantageous for surgically inserted implants a treatment site close to or surrounding highly sensitive and/or fragile nerves.

Although, the erosion rates of the gellan-xanthan hydrogel carrier matrices (scaffolds) appeared steady, higher pristine polymer particle content increased the initial and final stages of erosion. The difference in the erosion characteristics may be attributed to the differences in ionic charge of the individual polymers and the ionic interactions taking place between the polysaccharide matrix and the intercalated pristine PMMA particles at pH between about 5 and 9, particularly pH 7.4.

At pH 7.4 PMMA readily dissolved and the dissolved anionic PMMA particles readily formed a polyelectrolyte complex (PEC) with the cationic chitosan conferring the matrix with reduced swelling and erosion characteristics as observed.

No PEC is formed in the case of the hydrogel carrier matrices (scaffolds). With gellan-xanthan and PMMA both being anionic polymers, such ionic interactions are not possible and repulsion occurs between the similarly charged compounds. The action of repulsion and the influx of water into the gellan-xanthan gum blended matrices results in the dissolution of a large number of PMMA particles thereby contributing to the hastened erosion rate signified by mass loss of the matrix. Subsequent to erosion and loss of polymer mass, the lessened quantity of polymer matrix remaining is unable to absorb further water and undergo swelling compared to blends the slower eroding blending containing less PMMA particles, hence the stabilizing swelling profiles. The overall effect of PMMA inclusion into the hydrogel carrier matrices (scaffolds) is limiting the degree of swelling which is advantageous for applications involving treatment of injured peripheral nerves where excess swelling will exert unwanted pressure on a site of treatment and/or result in dislodgment from the site of treatment.

Furthermore, regarding the hydrogel carrier matrix, formulations containing higher gellan gum ratios underwent greater swelling with less erosion occurring over time. This may be due to the inherent swelling and erosion characteristics of the individual polymers. Xanthan gum absorbs water to initiate swelling ensuing polymer relaxation and disentanglement producing an apparent change in viscosity from a solid gel to fluid state causing its potential leakage from the matrix network. Gellan gum, being highly affinitive for instantaneous crosslinking with mono- and divalent ions is capable of producing rigid gels which may be further strengthened via subjection of the gel solution to temperatures above 90° C. Upon in vitro swelling and network pore enlargement, the previously crosslinked divalent ions may escape being replaced with the weaker monovalent ions from the dissolution media thereby unrestricting its water-uptake ability.

Determination of Molecular Vibration Transition Via FTIR Spectroscopy

The transitions in molecular vibrations resulting from pristine PMMA particle intercalation (dispersion) and ionic interactions were characterised using FTIR based on the percentage transmission. Furthermore, the evidence of crosslinking and interactions arising of the blending of the constituent polymers of the prepared chitospheres and hydrogel carrier matrices (scaffolds) were evaluated.

Chitospheres:

FTIR spectra of hydrated chitospheres show the formation of a new peak at 1540 cm$^{-1}$ (FIG. 6). This peak is in not present in the Control formulation; however, it increases in intensity as the concentration of pristine PMMA particles increase indicating increased formation of this particular bond representing polyelectrolyte complex (PEC) formation involving interactions between the positively charged amino groups of chitosan and the negatively charged carboxylic acids of PMMA.

Crosslinking is evident from the P=O vibrations occurring at 1150 cm$^{-1}$ as this indicates the quantity of bound sodium tripolyphosphate ions which form interchain links between the —NH$_3^+$ protonated groups of chitosan (Mi et al., 1999). The molecular integrity of the native polymer compounds, chitosan and PMMA, can be discerned. Chitosan maintains its OH stretching at 3200 cm$^{-1}$ and the peak at 1630 cm is indicative of its amino (—NH$_2$) bending vibration. The presence of PMMA is indicated by the C=O vibrations of the esterified carboxyl groups characterised by the strong peaks at 1700 cm$^{-1}$. The broad peak of chitosan at 3600 cm$^{-1}$ and the peak representing the amine bending at 1630 cm$^{-1}$ are evident in all of the formulations however with increase in the concentration of PMMA the intensity of these peaks decrease. On the contrary, the carboxylic acid peak of PMMA at 1700 cm$^{-1}$ is strongly detected in formulations 1:1 and 1:2, as these matrices contained the highest quantity of pristine PMMA particles, whereas a weak signal is produced in the 2:1 formulation.

Hydrogel Carrier Matrices (Scaffolds):

Regarding the formulation of hydrogel polysaccharide blends, both polymers (gellan and xanthan) exhibited a broad peak at 3263 cm$^{-1}$ and 3305 cm$^{-1}$ indicative of —OH stretching where the peak at 3305 cm$^{-1}$ presented the —OH groups of the glucopyranose ring in gellan gum (Verma and Pandit, 2012). Stretching vibrations of the —CH$_2$ groups occurred at wavelengths of 2892 cm$^{-1}$ for gellan gum. Xanthan gum produced a peak at 2882 cm$^{-1}$ relating to the axial deformation of C—H arising from the symmetrical and asymmetrical stretching of CH$_3$ and CH$_2$ groups and CHO groups (Faria et al., 2011). Bands appearing at 1600 cm and 1400 cm are due to the asymmetric and symmetric stretching of COO$^-$ groups in both polymers and where the presence of such bands is further indicative of C=O vibrations of enols and the deflection angle of C—H groups in xanthan gum, respectively (Faria et al., 2011). Defined bands occurring towards the end of the spectra at wavenumbers of 1020-1016 cm$^{-1}$ are characteristic of C—O stretching in both gellan and xanthan gum. The strong peak produced at 1722 cm$^{-1}$ distinguishes xanthan form gellan gum and is indicative of the C=O vibrations of carboxylic acids, esters, aldehydes and ketones (Faria et al., 2011). The presence of PMMA is identified by its esterified carboxylic acids groups peaking at 1700 cm$^{-1}$, however, when combined within the hydrogel carrier matrix formulations this peak overlaps with that corresponding to the carbonyls of xanthan gum. Calcium chloride (crosslinker) produces two distinct peaks occurring at 3389 cm$^{-1}$ and 1627 cm$^{-1}$.

Figure 7:
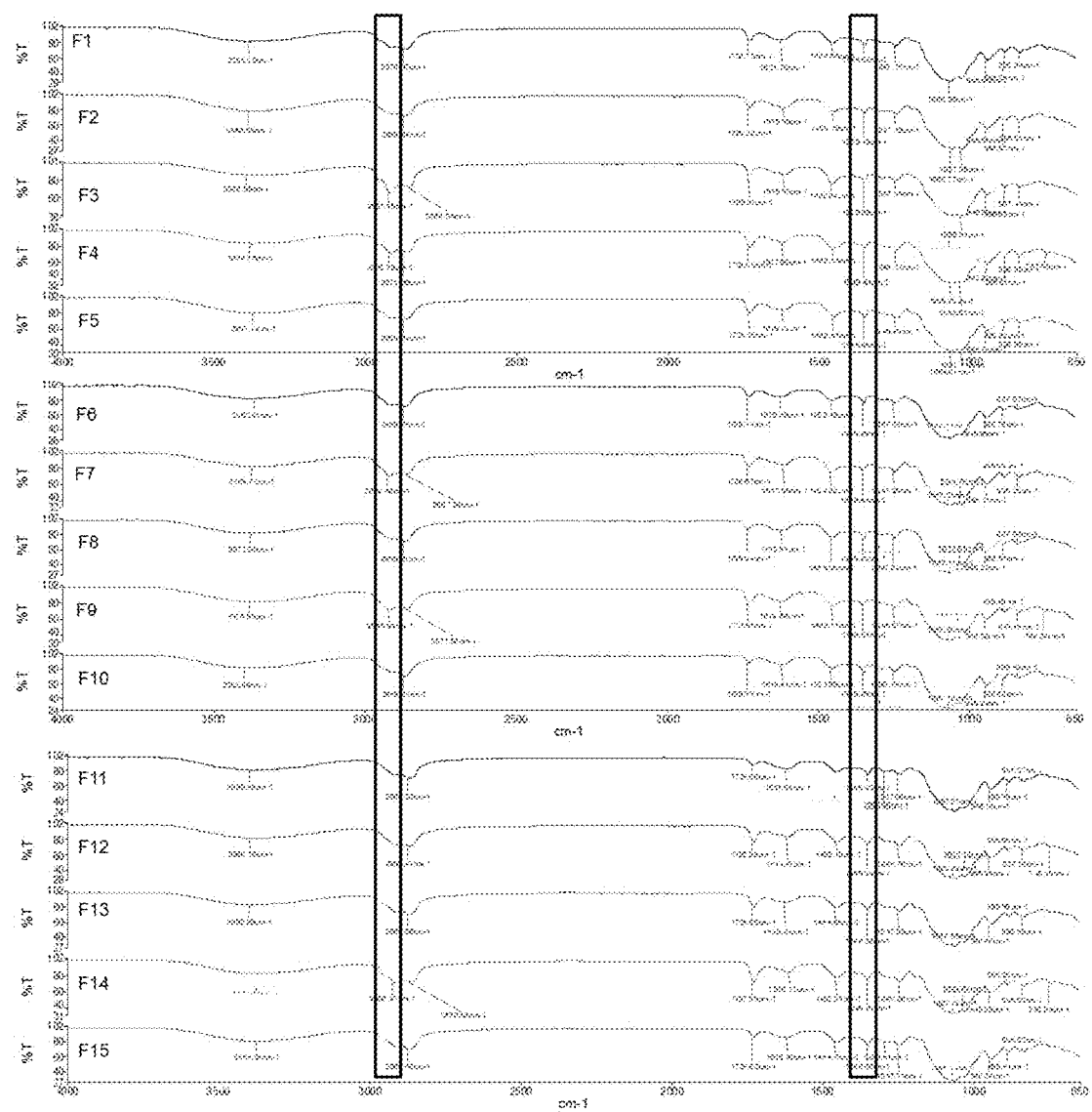
FIG. 7 shows FTIR spectra of the gellan-xanthan hydrogel carrier matrix Formulations 1 to 15.

The hydrogel gellan-xanthan gum hydrogel carrier matrices prepared as Formulations F1-F15 maintained the characteristic chemical compositions of the parent polymers (FIG. 7). Shifting of the peaks, corresponding to the vibrational stretching of —OH, CH$_2$, and COO$^-$ groups, towards higher wavenumbers indicated interaction of those functional groups with calcium. The formation a new peak at 2920 cm$^{-1}$ may indicate the presence of alkene methylene —CH$_2$ groups being formed from molecules of gellan and xanthan gum and possible containing calcium in its side chain. Ionic crosslinking within and between the individual polymers predominantly occurs via the ionic interaction of positive calcium ions with the negatively charged carboxyl COO$^-$ groups resulting in the formation of a calcium carboxylate salt (Verma and Pandit, 2012). The hydrogel blend may either be crosslinked from intermolecular linkages of calcium ions between two carboxylic acids of one polymer or the interchain linkages resulting in the connection of two carboxylic acid groups each from gellan and xanthan gum via a central calcium ion. The emergence of a new but weak band at 1349 cm-1 may be indicative of coordination of the COO$^-$ groups with calcium (Verma and Pandit, 2012). This method of non-covalent crosslinking may produce the formation of a semi-interpenetrating hydrogel network where one component is crosslinked in a polymer blend and where the constituent polymers are able to be separated without breaking of chemical bonds (Matricardi et al., 2013).

Texture Analysis

Matrix resilience (MR) refers to the ability of an object to recover to its original state after application of a force. It is also used as an indication of the presence of a porous matrix structure where the pores confer a sponge-like attribute to the matrix thereby allowing it to easily return to its original shape. Porous matrix structures have a higher MR compared to less porous and more compact matrices. The term 'compact' refers to a densely packed matrix network where minimal spaces are left between the polymer chains. Densely packed matrices are often brittle in nature and generally display low MR and high deformability moduli (DF) (matrix rigidity and flexibility) as they tend to resist any applied mechanical stress as opposed to dissipating the energy throughout the matrix to undergo deformation as with pliable matrix systems (Singh, 2007; Bawa et al., 2011).

Chitospheres:

Please Confirm that these Samples were HYDRATED Before Testing? the Hydration Forms the Pores as Per the Explanation Above. If not, Please Explain the Presence of Pores.

Hydrated chitosan matrices containing more poly(methacrylic-co-methyl methacrylate) (PMMA) particles presented with larger pores of a greater cumulative pore surface area and improved MR. Such a matrix, being more flexible, is able to absorb energy to undergo deformation and hence require more energy to rupture the chitospheres as opposed to compact less resilient matrices which resists the force applied until it breaks as indicated by the fracture energy (FE). FE was obtained as the amount of work done to initiate fracture of an object when a compressive stress is applied (Tanaka et al., 2005).

Hydrated chitosan-only matrices (excluding PMMA particles) exhibiting low a MR and high DF suggest that these multiparticulates are brittle. The FE, equating to the amount of energy in joules required to rupture a hydrated chitosphere, showed that the 1:1 chitospheres displayed superior strength however a trend was noted where an increase in PMMA content improved FE with such chitospheres requiring more energy than the Controls to rupture the matrix. FE decreases as the chitosphere matrix undergoes degradation over time.

Effects on MR imparted by PMMA pristine particle intercalation (dispersion) is observed in the chitospheres where the increasing resilience is attributed to the formation of pores upon the pH-responsive dissolution of the PMMA pristine particles.

Initially, during the first 2-5 days of exposure to pH 7.4 dissolution medium, the Controls and 2:1 chitospheres exhibited the highest MR compared to the 1:1 and 1:2 chitospheres, however, upon further exposure to PBS MR rapidly increases whereas that of the Control and 2:1 chitospheres gradually decreases. This increase in MR corresponds to pristine PMMA particles leaching resulting in the formation of pores which enhance the resilience of the chitospheres. The pristine PMMA particles act as a porogen.

Hydrogel Carrier Matrices (Scaffolds):

Textural analysis on hydrated hydrogel carrier matrices (scaffolds) provided insight into understanding the mechanism of swelling, degradation and drug release. Upon absorption of water, the hydrophilic matrices undergo various changes in mechanical properties depending on the concentration of crosslinker used and the total content of PMMA particles dispersed throughout the matrix. The penetration of water into the polysaccharide matrices initiates polymer chain relaxation and subsequent disentanglement of the polymer chains. Polymer disentanglement and chain relaxation allows the further influx of water into the core of the matrix. The movement of water in and out of the matrix allows the dissolution of the pristine PMMA particles thus creating a series of pore structures, either hollow or gelled core, via an in situ leaching out process.

The MR and DF values, as represented in FIG. 8, show that as the concentration of pristine PMMA particles increase it produced hydrogel carrier matrices (scaffolds) of higher MR and lower DF. This shows that hydrated matrices containing pristine PMMA particles are more resilient due to the formation of a porous matrix network hence its ability to recover after application of stress and undergo plastic deformation indicated by the low DF values. This increase in MR due to pore formation is validated by the SEM imaging and the porositometric analysis.

FIG. 9 shows the changes in textural properties when PMMA particles are embedded within an anionic polysaccharide hydrogel carrier matrix (scaffold). MR for all formulations gradually increases over time whereas deformation and fracture energy decreases as water penetration, swelling and erosion occur.

Formulations containing higher concentrations of particles displayed superior MR, particularly F4, F5 and F14 containing 0.75 g/g of pristine particles and F7 and F12 synthesised with 0.50 g/g of PMMA particles. At the end of the study period, these formulations exhibited resilience values between 45-56% compared to formulations containing 0.25 g/g of PMMA particles displaying resilience values between 31-40%. The observed increase in matric resilience conferred by the pH-responsive particulate leaching of the PMMA particles for the formation of pores corresponds to the loss in weight of the hydrogel carrier matrix (scaffold). F4, F5, F12 and F14 exhibited the highest erosion rates possibly due to the loss of PMMA particles from the matrix resulting in less polymer materials remaining at the various sampling points. As erosion continues, deformation and fracture energy decrease as the matrix loses bulk weight and weakens thus indicating loss of rigidity of the network. Weak matrix network requires less energy to cause a break in the system hence the declining fracture energies.

Furthermore it is noted that the ratios of gellan and xanthan gum and the crosslinker concentration influence the textural properties of the hydrogel carrier matrices (scaffolds), specifically deformation and fracture energy. Formulations containing higher ratios of gellan gum and calcium chloride, 4 parts gellan to 1 part xanthan and 0.1% w/v crosslinker, displayed high fracture energies and low matrix flexibility. Increased gellan and calcium quantities produce brittle hydrogel carrier matrices (scaffolds) which crack upon application of a force due to resistance of the force rather than distributing the applied energy throughout the matrix to undergo plastic deformation. Xanthan modifies the hardness of the hydrogel carrier matrix (scaffold) offering a method for achieving a fine balance between flexibility and rigidity. Xanthan gum, widely used as a rheology modifying agent in the food industry, swells to form a highly viscous gel which contributes to the resilience and pliability of the hydrogel carrier matrices (scaffolds).

SEM

Chitospheres:

The surface morphology of the Control chitosan matrices were found to be fairly smooth in comparison to those containing pristine PMMA particles whereas closer inspection of the surface of PMMA-containing matrices revealed a rough surface where the presence of PMMA particles is clearly noted on the matrix surface. SEM images of the degraded matrix samples were taken at 1, 2 and 5 days after exposure to PBS (FIG. 10). Chitosan matrices containing pristine PMMA particles maintained their spherical shape and most of the structural integrity compared to the Control samples which appeared cracked and fragmented and the 2:1 chitospheres samples, which underwent a slight change in shape. This may suggest that not only does the addition of pristine PMMA particles enhance the mechanical strength of the chitospheres but a polyelectrolyte complex (PEC) may be formed upon hydration between the cationic chitosan and anionic PMMA producing chitospheres that are robust in their structural shape. An array of pores is evident on the surface of chitospheres containing larger quantities of pristine PMMA particles, namely the 1:1 and the 1:2 chitospheres. These pores are probably formed from the dissolution and leaching out of the intercalated pristine PMMA particles; as such pore structures cannot be identified on the chitosan-only chitospheres. Furthermore, it is noted that the 2:1 chitospheres and, upon closer inspection, the 1:1 and 1:2 chitospheres underwent a process of detachment of the outermost layer. This suggests the occurrence of initial surface erosion whereas the Control chitospheres, which does not exhibit this trait of surface flaking, may degrade by bulk degradation of the matrix (Zhang et al., 2002).

Hydrogel Carrier Matrices (Scaffolds):

SEM cross-section morphology, shown in FIG. 11, reveals the appearance of large honeycomb-like macroporous structures post-dissolution and lyophilisation of the hydrated hydrogel carrier matrices (scaffolds). The presence of this large porous network further enhances the resilience of the hydrogels and improves its water holding capacity.

Thermal Studies
Chitospheres:

The DSC curves show that chitospheres cured in stronger sodium tripolyphosphate solutions required more heat to initiate melting. The melting points of the chitospheres increased when a 2:1 ratio of chitosan:PMMA was used. However, further increase in the PMMA concentration caused a decrease in the melting points with the exception of chitospheres prepared in a 1% w/v sodium tripolyphosphate solution. PMMA (Eudragit S100) has a melting point of 220° C. whereas chitosan exhibits the onset of melting at about 270° C. When the concentration of PMMA exceeds that of chitosan, the onset of melting decreases since PMMA is abundantly present in the chitosphere matrix. Regardless of the concentration of sodium tripolyphosphate used, 1:2 chitospheres exhibited similar melting points (FIG. 12).

Figure 14:
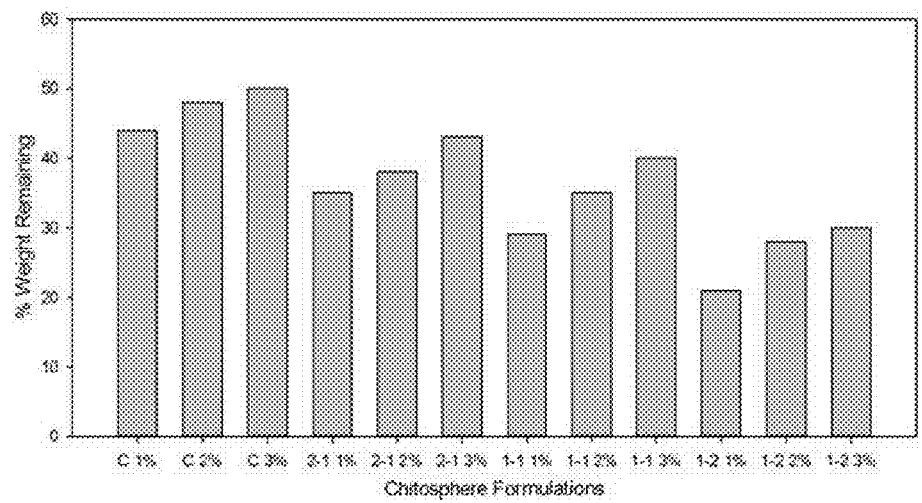
FIG. 14 shows a graphic representation of % weight remaining after thermal degradation of the various chitosphere formulations and controls at a temperature of 900° C.

The TGA thermograms showed the degradation of chitospheres in 3 steps whereas the degradation of the Control multiparticulates occurred in 2 steps. Between 264.45° C. and 900° C. chitosan exhibited a decrease in weight from 11.02% to 90% with 10% of the weight remaining at 900° C. The degradation of PMMA started at 284° C. where 94.035% of the sample remained but this quickly declined to 7.984% at 448.08° C. and at the 540° C. complete degradation took place. The first step in the thermal degradation of the chitospheres ranging from 100-190° C. was probably due to the loss of residual water as only a 2% loss in weight was observed. The second stage of degradation was noted in the temperature range of 266-380° C. where 30-40% weight loss was noted. This may be due to the decomposition of chitosan in the matrix whereas a combination of chitosan and PMMA decomposition may have occurred in matrices comprising pristine PMMA particles. The final stage of degradation occurring after 450° C. pertains only to the pristine particle-loaded chitospheres and demonstrates a further weight loss of 50-60% of its initial weight. This most likely indicated the decomposition of PMMA particles as decrease in weight was particularly noted in samples containing higher ratios of pristine PMMA particles to chitosan. At each thermal degradation stage outlined, increase in sodium tripolyphosphate crosslinker enhanced the thermal stability of the chitospheres. This can be seen in FIG. 14 which shows the % weight remaining at 900° C. signifying the end of the run. The chitosan-only multiparticulates demonstrated the least loss in weight denoting that it has a higher thermal stability compared to those chitospheres containing pristine PMMA particles which apparently weaken the matrices' thermal stability and accelerates its heat degradation.

Hydrogel Carrier Matrices (Scaffolds):

Gellan-xanthan blending, its ionic crosslinking and the intercalation of PMMA particles thereof, resulted in different thermal characteristics compared to intercalation with a pure chitosan for the chitospheres. DSC and TGA were employed in addition to FTIR spectroscopy to further validate the formation of crosslinks resulting in a gellan-xanthan hydrogel interpenetrating network (IPN) by measuring the changes in energy transfers and mass polymer decomposition. The first endothermic peak in the DSC thermograms appearing around 100° C. is probably the presence of crystalline water entrapped between the polymer chains. No defined melting peaks were observed in both the native polysaccharides and the formulations. Gellan gum displays its exothermic peak at 253° C. whereas Xanthan gum exhibits an exothermic peak at 282° C. indicating its superior thermal stability compared to gellan. The DSC thermogram of PMMA shows two endothermic peaks: a weak peak at 93° C. which may be attributed to the evaporation of moisture residues and a prominent peak at 220° C. were melting is initiated. The broad exothermic peak occurring towards the end of the experimental run around 270° C. indicates polymer decomposition; however this peak exhibited significant changes in intensity with varying concentrations of crosslinker and thus provides validation and determination of the degree of crosslinking. It was noted that increase in $CaCl_2$ concentration generally resulted in decreased height and area of the exothermic peak suggesting calcium-polymer bond formation resulting from the $Ca^{2+}$ cation chelation of anionic carboxylates thus improving thermal stability of the formulations via formation of a more rigid matrix network. The energy associated with this phase of degradation provides an indication of the ease of bond-breaking and hence the crosslinking degree. Highly crosslinked matrices require greater temperatures for the initiation of thermal decomposition thereby giving off less energy due to a smaller number of bond-breakage at that specific temperature. Increase in $CaCl_2$ concentration from 0.05% w/v to 0.1% w/v across the three different gum ratios increased the temperature at which the exothermic peak appeared hence increasing the temperature of the onset of degradation. Moreover, this decomposition stage resulted in the release of less energy, at that particular temperature range, which equates to less bond-breakage ensuing in the polymer matrix during thermal degradation. The improved thermal stability arises from ionic bonds between calcium cations and carboxylate anions present in gellan and xanthan gum. Comparing the parent polymers, although the temperature corresponding to the onset of degradation remained similar, the enthalpy change during polymer disintegration decreased from 1684mJ and 1240mJ for gellan and xanthan gum, respectively, to values in the range of 91-192mJ in the various hydrogel formulations where increased concentration of crosslinker decreased the change in energy transferred. This indicates that the unmodified polymer powders underwent extensive thermal degradation due to absence of crosslinks compared to the crosslinked hydrogel interpenetrating networks (IPNs).

In addition, the glass transition temperature (Tg) may be used to provide an indication of crosslinking, crystallinity and homogeneity of the constituent polymer components. The presence of only one Tg including a single exothermic peak indicates the formation of a homogenous crosslinked IPN matrix whereas basic polymer blends would result in the emergence of multiple distinct glass transition temperatures each corresponding to the individual constituent polymers. Increase in crystallinity is reflected by a larger and broader glass transition whereas increase in crosslinking shifts the Tg to higher temperatures. The Tg of gellan and xanthan gum were not evident in the experimental run and may possibly occur at temperatures lower than zero. However, well-defined glass transitions, peaking at around 20° C., of the crosslinked formulations were evident on the thermograms indicating the presence of crosslinks and the formation of a partly rigid matrix structure. Furthermore, a slight endothermic dip noted in the thermograms between 220-230° C. prior to the onset of polymer decomposition may be indicative of PMMA melting as formulations containing higher PMMA concentrations ranging from 0.5 g-0.75 g/g present with a slightly pronounced endothermic slope.

The TGA thermograms in conjunction with the derivatisation curves were correlated to the results obtained from DSC. As noted in DSC, all TGA thermograms presented with an initial minimal decomposition step which corresponded to the dehydration process of entrapped crystalline water molecules. Pure gellan and xanthan gum underwent the greatest loss in weight at temperatures of 270° C. and 295° C., respectively, corresponding to the polymer decomposition indicated by the exothermic peak in DSC with complete decomposition occurring at 615° C. for gellan whereas an 8% mass of xanthan remained at the end of the 900° C. run. According to the derivatisation curves, a further decomposition step occurred peaking at 606° C. and 634° C. for gellan and xanthan, respectively. PMMA exhibited two decomposition steps: at 237° C. where less than 5% weight loss occurred indicative of polymer melting and at 395° C. which was indicative of polymer decomposition with complete sample degradation occurring at 434° C. CaCl2 exhibited the first decomposition peak at 190° C. pertaining to the decomposition of chloride with a steady 39% remaining mass towards the end temperature of 900° C. According to literature, calcium only melts at 840° C. explaining the flat linear portion of the thermogram starting from 280° C. onwards indicating only slight changes in sample weight.

TGA thermograms of the experimental formulations exhibited decomposition in 4 steps: Step 1 occurring between 80-100° C. corresponds to the loss of residual moisture from the samples; Step 2 occurring between 250-260° C. and ending at 350° C. was attributed to polysaccharide degradation where the major loss of sample weight was observed; Step 3 initiating at approximately 395-399° C. and ending at 436° C. was due to the decomposition of the pristine polymer particles; Step 4 was assigned to the final stage of polymer degradation and occurred in the range of 570-580° C. Analysis of the derivatisation curves revealed that the most significant change in weight of the samples occurred at Step 2 and Step 4. The peak corresponding to Step 3 fluctuated in intensity in response to increases and decreases in the concentration of PMMA particles. From the derivative curve, it was further noted that highly crosslinked formulations, F1, F3, and F15 containing 0.1% w/v CaCl2 and F8 and F11 containing 0.075% w/v CaCl2 presented with a new peak at 319° C. shouldering off the Step 2 decomposition peak. This may indicate the decomposition of calcium carboxylate salt in the form of carboxylate-Ca-carboxylate crosslinks.

Porosity

Figure 10:
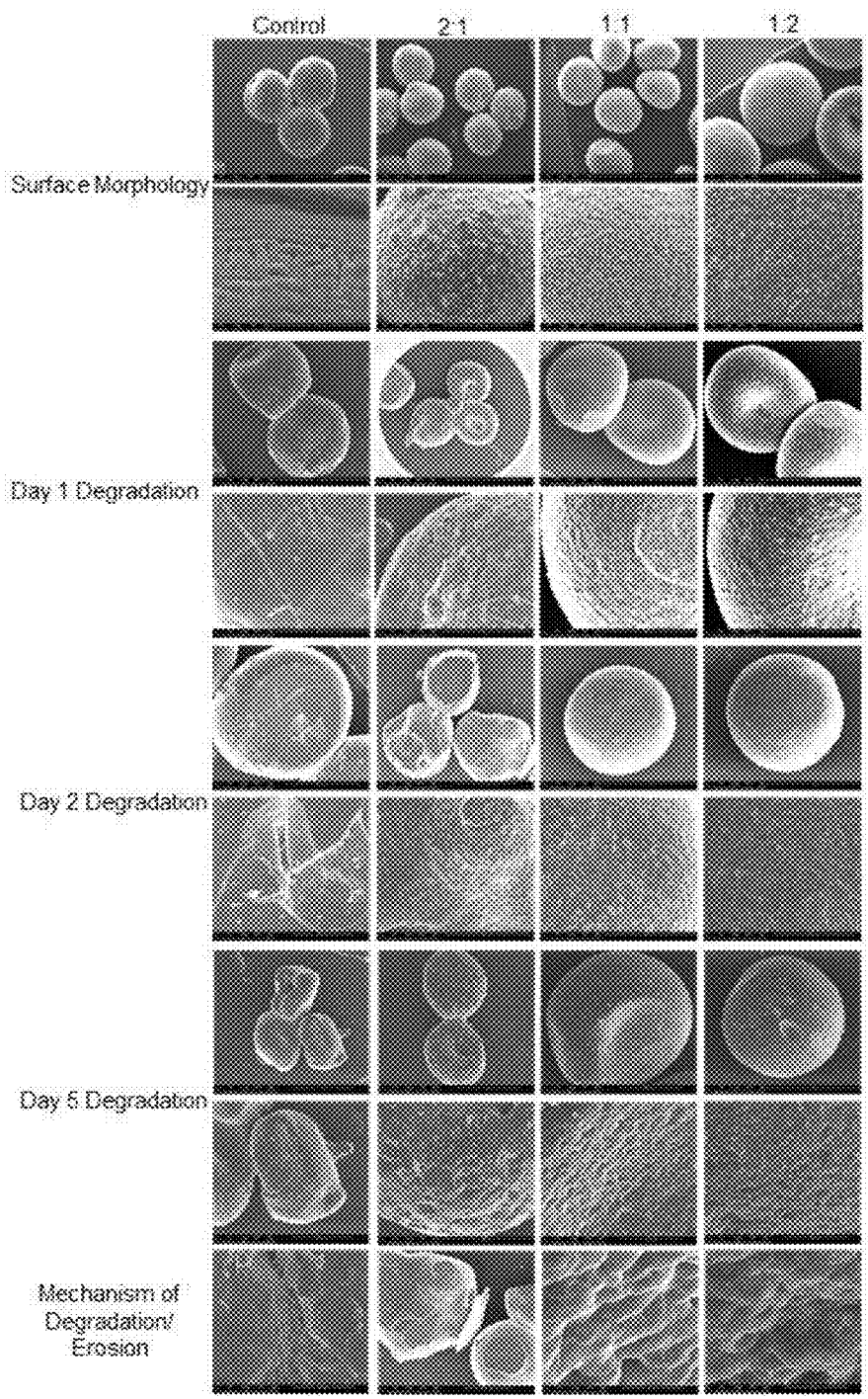
FIG. 10 shows SEM images depicting the surface morphology of the chitospheres and their appearance at Days 1, 2 and 5 after degradation studies.
Figure 13:
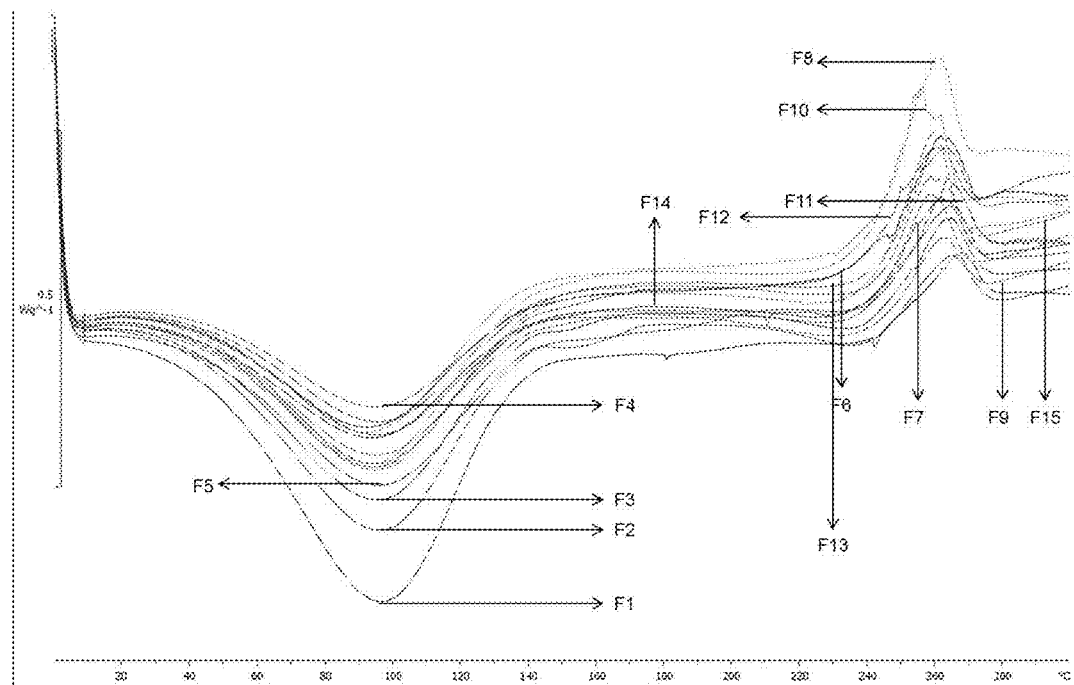
FIG. 13 shows DSC thermograms of the crosslinked gellan-xanthan hydrogel carrier matrix Formulations 1 to 15.

Chitospheres:

Porositometric analysis of chitosan matrices hydrated in pH 7.4 dissolution medium revealed the differences in surface area, pore size and pore volume when matrices are prepared with varying concentrations of PMMA particles. The results show that the Controls (PMMA-particle free matrices) exhibited a high surface area but a smaller pore size and cumulative pore surface area compared to the chitospheres. The 1:1 chitospheres contained the largest pores and smallest surface area. Increasing the PMMA-particle content decreases the total surface area and increases pore size in terms of pore width, diameter and volume. The pore size and volume reflects the cumulative surface area of pores on the sample where pores larger in diameter and depth contribute to a larger pore surface area but smaller BET total surface area. However, further increase in PMMA-particle concentration (1:2 chitospheres) relative to chitosan results in a slight decline in pore size with a BET surface area similar to that of the 2:1 chitospheres. The lower BET surface areas of the chitospheres compared to that of the Controls, despite formation of pores, may further suggest that pore formation occurs only on the surface of sphere (as visualised by SEM) and not throughout the entire sphere which would result in an apparent increase in the total surface area of the sample. Although exhibiting a lack of pores, the significantly larger surface area of the Control multiparticulates, 25.5898 $m^2/g$, may be contributed by the formation of cracks on the surface as imaged by SEM in FIG. 10. The technique of nitrogen gas adsorption over a range of relative pressures for the determination of pore characteristics produce adsorption isotherms which provide insightful information regarding the pore size distribution in terms of pore width categorised as micro-(<2 nm), meso- (2-50 nm) and macropore (>50 nm) ranges (Sing et al., 1985; Groen et al., 2003). According to this classification, the pore size distribution of the chitospheres lies within the mesopore range. The control matrices and the 2:1 chitospheres presented a Type II isotherm with a H2 hysteresis loop indicating an unrestricted monolayer-multilayer adsorption of a nonporous adsorbent. The 1:1 and 1:2 chitospheres exhibit a Type IV isotherm, indicating existence of a multilayer material, with a H3 hysteresis loop suggestive of complete pore filling including capillary condensation which occurs in the presence of mesopores (Sing et al., 1985; Groen et al., 2003). The presence of a H2 and H3 hysteresis loop denotes an interconnected pore system of random distribution within the chitosphere matrix (Groen et al., 2003). The initiation of the shift from a Type II isotherm and H2 hysteresis towards a Type IV isotherm and H3 hysteresis is seen, corresponding to the isotherm generated for the 2:1 chitospheres where the PMMA particles, in the lowest concentration, are introduced.

Hydrogel Carrier Matrices (Scaffolds):

Porositometric analysis performed in accordance to the BET and BJH models, using nitrogen as the adsorptive gas, was used to ascertain the pore size, pore surface area and shape by assessing the shape of the isotherm and resulting hysteresis loop. Presence of hysteresis indicates the presence of pores whereas its shape may assist in determining pore shape. Formulations, after 24 hours of dissolution, containing higher concentrations of PMMA particles presented with greater BET surface and micropore areas as a result of multiple empty impressions left behind after the in situ porogen leaching effect of the intercalated particles. The pores formed by the dissolution of the PMMA particles measure between 2-3.6 nm indicating a pore size distribution within the mesopore range. In addition, such formulations exhibited slightly larger pore volumes and pore diameters compared to formulations containing less PMMA particles. Type II and IV isotherms were noted for formulations comprising 70:30 and 60:40 gum ratios, respectively, whereas F14 composed of an 80:20 polymer ratio and 0.75 g/g PMMA particles featured a Type II isotherm while 0.25 g/g PMMA particle intercalation presented a Type IV isotherm. The presentation of H3 and H4 hysteresis may suggest a varying slit-like ranging to a conical-like shape of the pores.

In Vitro Drug Release

Drug release occurs by three primary mechanisms as described by Yao and associates (2011): 1) diffusion-controlled, 2) swelling-controlled and 3) chemically-controlled. The chemically-controlled drug release mechanism encompasses surface erosion, bulk degradation and other interactions or processes taking place within the polymer matrix. It may be possible that one or more of these release mechanisms could be occurring simultaneously within a matrix system or one may be the dominant mechanism at certain stages of matrix hydration and erosion.

Figure 15:
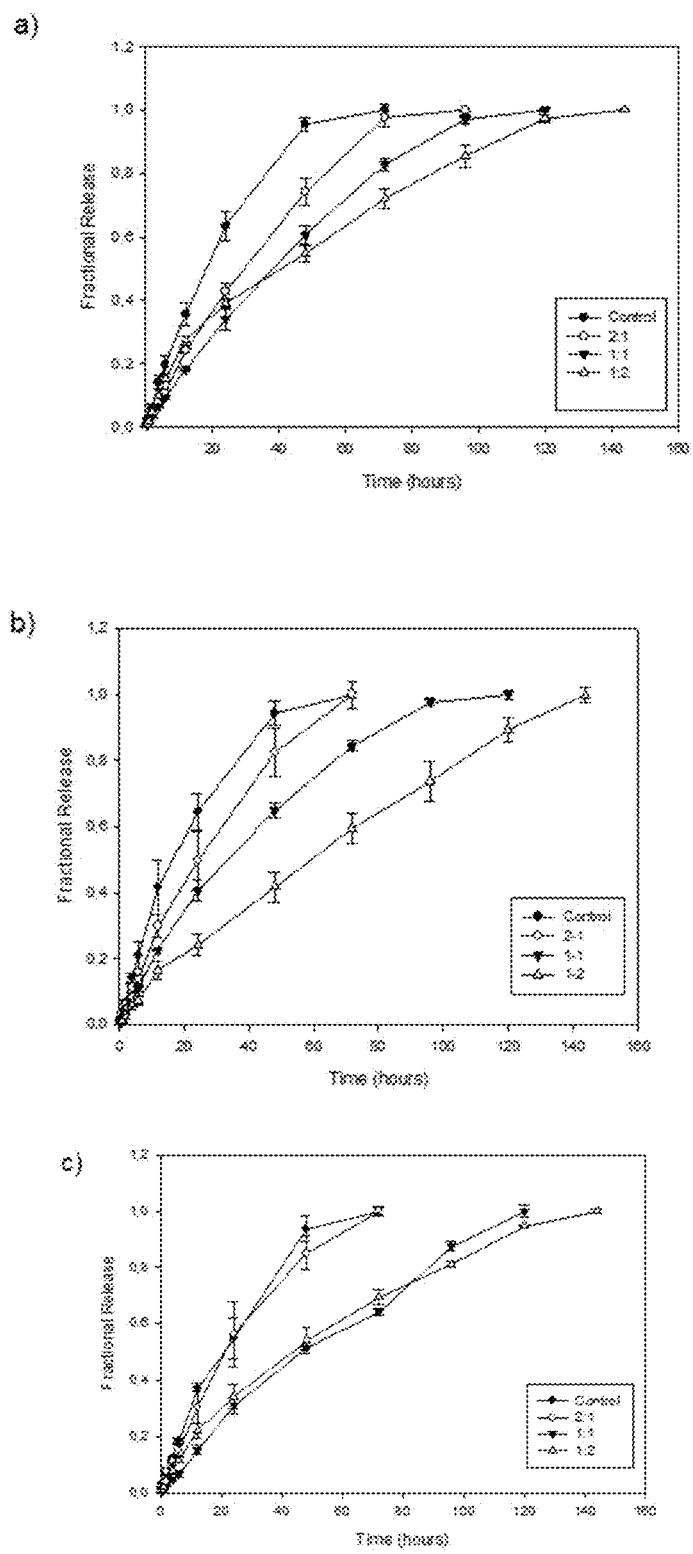
FIG. 15 shows API/drug-release profiles of the various chitospheres formulations indicating the effect of pristine PMMA particles concentration on the drug-release rate a) 1% w/v sodium tripolyphosphate b) 2% w/v sodium tripolyphosphate c) 3% w/v sodium tripolyphosphate.

Chitospheres:

The different chitospheres formulations were able to provide complete and sustained release of indomethacin in a linear manner. From the release profiles depicted in FIG. 15 it is evident that the addition of pristine PMMA particles to the chitospheres matrices were able to prolong the drug release rate where increase in pristine poly(methacrylic-co-methyl methacrylate) (PMMA) particles concentration lead to a reduction in the rate of drug release. The Control matrices, formulated from only chitosan, provided release up till only 72 hours whereas chitospheres containing pristine PMMA particles exhibited release profiles extending over 144 hours where the former was observed for chitospheres crosslinked in a 2% w/v sodium tripolyphosphate solution. Although increase in the concentration of crosslinking solution used demonstrated a decrease in the release rates, the difference in this reduction was very little as the plotted drug release curves were often superimposable. Burst release has been defined as the immediate and large release of drug molecules from a delivery system within 24 hours of exposure to dissolution medium (Huang and Brazel, 2001). Significant burst release was not noted during the first sampling point however, after 24 hours, chitospheres released less drug compared to the Control formulation which released between 55-64% of the incorporated drug within the first 24 hours. As the concentration of PMMA increased the total amount of drug released at 24 hours considerably decreased with the 2:1 chitospheres releasing 42-56%, the 1:1 chitospheres releasing 31-40%, and the 1:2 chitospheres releasing only 25-39% of the total encapsulated drug.

Without being limited to theory, the in situ formation of a polyelectrolyte complex (PEC) aided in prolonging API/drug release when in use. The above is advantageous in the treatment of nerve injuries where prolonged release of API/drug is advantageous for healing and/or reduces the need for repeat surgical procedures to insert biodegradable implants.

All the chitosphere formulations and the Control initially release drug via diffusion as the drug molecules located on the peripheral region of the sphere as the sphere hydrates and dissolutes into the surrounding media via a concentration gradient. A burst release of drug was not observed and was possibly due to washing of the spheres in 1M acetic acid to remove surface drug and unreacted polymer.

As the PMMA containing chitospheres continue to hydrate the PEC forms the outer shell and the outer shell undergoes a transition from a glassy to a rubbery state (Yao et al., 2011). Drug molecules in the hydrated rubbery layer of the chitospheres are free to dissociate from the matrix and diffuse out whereas molecules located in the unhydrated glassy core remain static. A combination of erosion, swelling and chemically-based release may occur with chitospheres containing pristine PMMA particles. Chitospheres are proposed to release drug by an in situ leaching process where the pristine PMMA particles act as the porogen. PMMA, being a pH-responsive polymer, dissolves at a typical pH higher than 7.0. When the chitospheres are exposed to PBS of pH 7.4, the same pH-responsive dissolution is considered to take place leaving behind porous structures in its place.

Furthermore, since PMMA dissolves in the PBS, the dissolved matter remains in the chitosan matrix thereby initiating the formation of a PEC between the cationic chitosan the dissolved molecules of the pristine PMMA particles. Since chitosan is a cationic polymer and PMMA an anionic polymer it is likely that some electrostatic interactions may have arisen resulting in the formation of a PEC with binding occurring between the positively charged amine and negatively charged carboxyl groups of chitosan and PMMA, respectively, leading to the synthesis of a carboxylate functional group indicated by the new peak formed at 1540 cm$^{-1}$ as depicted in the FTIR spectra (Li and Huang, 2012). However, since the unreacted amine and carboxylic acid functional groups corresponding to the native polymers of chitosan and PMMA, respectively, are still present it suggests that only a certain ratio of these molecules reacted to form a new bond. It may be possible that parts of the PMMA particle may still be residing in a partially empty pore while the surface around this particle forms a PEC. Since the intensity of the new peak at 1540 cm$^{-1}$ is far less than the native peaks it may suggest that the PEC is present small quantities.

It is noted that unhydrated chitospheres also display this new peak although a very weak signal is produced; particularly when the crosslinker concentration is increased, this peak becomes hardly evident. However, after hydration of the matrices in PBS pH 7.4, the intensity of the peak significantly increases. This presence of this peak in the unhydrated spheres is due to the alkaline pH of the crosslinking solution. However, the increase in the intensity of the 1540 cm$^{-1}$ peak from the unhydrated to the hydrated chitosphere matrices, as observed in FTIR, proves the spontaneous, largely in situ synthesis, of a PEC between these oppositely charge polymers. Furthermore, the weak thermal stability of unhydrated chitospheres suggests the presence of unreacted PMMA particles validating that PEC synthesis takes place only upon hydration. This formation of a PEC may explain the reduced swelling and the prolonged and slowed drug release rates. Moreover, the retention and entanglement of drug in the PEC regions further retard drug release.

Hydrogel Carrier Matrices (Scaffolds):

The crosslinked gellan-xanthan gum hydrogel carrier matrices (scaffolds) (i.e. Formulations 1-15) were able to sustain the release of the model protein, bovine serum albumin (BSA), for until 15 or 20 days (FIG. 16). Thereafter, no further BSA was detectable. Formulations 2, 4, 5, 6 and 9 released between 45-50% of the total incorporated protein whereas F1, F3, and F13 released more than 50% and F7, F8, F10, F11 and F14 releasing between 60-67% of the total protein. At the end of 15 days, F12 released the lowest amount of protein, 37%, and F15 released the highest amount of 75%. Formulation 15, releasing the highest amount of BSA also exhibited the fastest release rate which corresponds to its high degree of water-uptake and swelling. Formulation 12 displayed the slowest release rate conferred by the equally slowed rate of water penetration and swelling. Similar release kinetics were observed with the release of diclofenac sodium however, the release of diclofenac sodium from all the formulations was significantly retarded with only 14-20% of the total drug being released over 30 days (FIG. 17).

The inclusion of pristine PMMA particles assisted in reducing the drug release rates for both BSA and diclofenac sodium. The slowed release rates imparted by the intercalation of pristine PMMA particles are seen particularly in Formulations F4 and F9 where drug release is dependent on water penetration into the matrix, hydration of the PMMA particles and subsequent dissolution of PMMA out of the matrix. The release rate of F4 corresponds to the reduced water-uptake and swelling. Formulations 1, 3, 5 and 15 containing the highest concentration of crosslinker displayed faster release rates which were mostly due to the enhanced swelling of the matrix, particularly F1 and F15 which underwent the greatest swelling and size change. Faster dug release rates in the presence of increased CaCl$_2$ concentrations may attributed to the formation of intramolecular complexes between calcium ions and the pyruvate moiety of xanthan gum leading to collapse of the sidechains into the polymer backbone thereby decreasing the hydrodynamic volume of the polymer chains when a rigid orderly conformation is adopted. This intramolecular interaction and chain conformation results in the formation of large network pores which facilitate water and drug diffusion through the matrix. Moreover, the exchange of excess calcium ions with weaker monovalent ions present in the dissolution medium and the pronounced electrostatic repulsion between anionic side chains of the polymers may have resulted in uncontrolled swelling thus allowing the escape of drug molecules via diffusion through the enlarging meshwork between the polymer chains of the gel matrix as swelling and network expansion continued. The erosion associated with the inclusion of pristine polymer particles did not affect the drug release rates, since upon the dissolution of the particles drug molecules remained within the gel matrix and slowly diffused out through the pores as the hydration interface expanded. Decreased drug release rates were noted with formulations containing higher ratios of xanthan gum. In these cases, the viscosity change of xanthan gum associated with its water-uptake and swelling combined with the pH-responsive particulate leaching contributed to the formation of gelled-filled channels and pore structures. These gel-filled spaces retarded the diffusion-driven movement of drug molecules out of the matrix thus retaining the drug particles in a gel-suspension within these voids.

CONCLUSIONS

The invention provides for a biodegradable implant comprising a hydrogel carrier matrix (scaffold) having dispersed therein a multitude of spheroidal particles, each of the hydrogel carrier matrix and the spherical particles may be API/drug loaded.

The biodegradable implant according to the invention showed the advantages of decreased swelling, prolonged drug release and enhanced mechanical properties specifically matrix resilience and flexibility imparted by the pH-responsive dissolution of the particles. The inclusion of PMMA particles into the hydrogel carrier matrix and/or the spherical particles contributed to the observed and discussed advantages.

Furthermore, the tuning of matrix rigidity and flexibility may be attained via variation of xanthan gum composition in the hydrogel formulation. In addition, the ionic crosslinking of the hydrogel blends forming an interpenetrating network provides the appropriate attributes of a tissue repair material offering a network of suitable mechanical properties for tissue compatibility and the concurrent sustained release of proteins and drug molecules. The study further validates the in situ particulate leaching and simultaneous polyelectrolyte complexation with cationic materials producing matrices where enhanced strength in terms of matrix hardness is required with the prolonged drug release rates.

The Applicant believes that the biodegradable implant according to the invention at least ameliorates one disadvantage known in the prior art and/or described herein above.

While the invention has been described in detail with respect to specific embodiments and/or examples thereof, it will be appreciated that those skilled in the art, upon attaining an understanding of the foregoing may readily conceive of alterations to, variations of and equivalents to these embodiments. Accordingly, the scope of the present invention should be assessed as that of the appended claims and any equivalents thereto.

REFERENCES

Bawa, P., Pillay, V., Choonara, Y. E., du Toit, L. C., Ndesendo, V. M. K., and Kumar, P., (2011). A Composite Polyelectrolytic Matrix for Controlled Oral Drug Delivery. *AAPS PharmSciTech*, 12(1), 227-238.

Cobianchi, S., Casals-Diaz, L., Jaramillo, J., and Navarro, X., (2013). Differential effects of activity dependent treatments on axonal regeneration and neuropathic pain after peripheral nerve injury. *Experimental Neurology.* 240, 157-167.

Conti, A. M., Brimijoin, S., Miller, L. J., and Windebank, A. J., (2004). Suppression of neurite outgrowth by high-dose nerve growth factor is independent of functional p75NTR receptors. *Neurobiology of Disease,* 15, 106-114.

Coutinho, D. F., Sant, S. V., Shin, H., Oliveira, J. T., Gomes, M. E., Neves, N. M., and Reis, R. L., (2010). Modified Gellan Gum hydrogels with tunable physical and mechanical properties. *Biomaterials,* 31(29), 7494-7502.

Faria, S., de Oliveira Petkowicz, C. L., de Morais, S. A. L., Terrones, M. G. H., de Resende, M. M., de Franca, F. P., and Cardoso, V. L., (2011). Characterization of xanthan gum produced from sugar cane broth. *Carbohydrate Polymers,* 86(2), 469-476.

Goodman, L. S., and Gilman, A. G., (2008), "General Principles", in Brunton, L. L., Parker, K. L., Blumenthal, D. K., and Buxton, I. L. O. (eds), *Goodman & Gilman's Manual of Pharmacology and Therapeutics*, USA: McGraw-Hill Companies, pp. 1-43.

Groen, J. C., Peffer, L. A., and Pérez-Ramírez, J., (2003). Pore size determination in modified micro- and mesoporous materials. Pitfalls and limitations in gas adsorption data analysis. *Microporous and Mesoporous Materials,* 60(1), 1-17.

Huang, X., and Brazel, C. S., (2001). On the importance and mechanisms of burst release in matrix-controlled drug delivery systems. *Journal of Controlled Release,* 73, 121-136.

Jain, D., Panda, A. K., and Majumdar, D. K., (2005). Eudragit S100 entrapped insulin microspheres for oral delivery. *AAPS Pharmscitech*, 6(1), E100-E107.

Kachrimanis, K., Ktistis, G., and Malamataris, S., (1998). Crystallisation conditions and physicomechanical properties of Ibuprofen-Eudragit® S100 spherical crystal agglomerates prepared by the solvent-change technique. *International Journal of Pharmaceutics*, 173(1), 61-74.

Kemp, S. W., Webb, A. A., Dhaliwal, S., Syed, S., Walsh, S. K., and Midha, R., (2011). Dose and duration of nerve growth factor (NGF) administration determine the extent of behavioral recovery following peripheral nerve injury in the rat. Experimental neurology, 229, 460-470.

Khan, M. Z. I., Stedul, H. P., and Kurjakovic, N., (2000). A pH-dependent colon-targeted oral drug delivery system using methacrylic acid copolymers. II. Manipulation of drug release using Eudragit® L100 and Eudragit S100 combinations. *Drug Development and Industrial Pharmacy,* 26(5), 549-554.

Li, J., Huang, Q., 2012. Rheological properties of chitosan-tripolyphosphate complexes: From suspensions to microgels. Carbohydr. Polym. 87, 1670-1677.

Malafaya, P. B., Silva, G. A., and Reis, R. L., (2007). Natural-origin polymers as carriers and scaffolds for biomolecules and cell delivery in tissue engineering applications. *Advanced Drug Delivery Reviews,* 59(4), 207-233.

Matricardi, P., Di Meo, C., Coviello, T., Hennink, W. E., and Alhaique, F., (2013). Interpenetrating polymer networks polysaccharide hydrogels for drug delivery and tissue engineering. *Advanced Drug Delivery Reviews,* 65(9), 1172-1187.

Mi, F. L., Shyu, S. S., Lee, S. T., Wong, T. B., 1999. Kinetic study of chitosan-tripolyphosphate complex reaction and acid-resistive properties of the chitosan-tripolyphosphate gel beads prepared by in-liquid curing method. J. Polym. Sci. B. Polym. Phys. 37, 1551-1564.

Paharia, A., Yadav, A. K., Rai, G., Jain, S. K., Pancholi, S. S., and Agrawal, G. P. (2007). Eudragit-coated pectin microspheres of 5-fluorouracil for colon targeting. *AAPS PharmSciTech,* 8(1), E87-E93.

Shenvi, S., Ismail, A. F., Isloor, A. M., 2014. Preparation and characterization study of PPEES/chitosan composite membrane crosslinked with tripolyphosphate. Desalination 344, 90-96.

Shu, X. Z., Zhu, K. J., 2002. Controlled drug release properties of ionically cross-linked chitosan beads: the influence of anion structure. Int. J. Pharm. 233, 217-225.

Sing, K. S., (1985). Reporting physisorption data for gas/solid systems with special reference to the determination of surface area and porosity (Recommendations 1984). *Pure and Applied Chemistry,* 57, 603-619.

Singh, A., Sharma, P. K., and Malviya, R., (2011). Release behavior of drugs from various natural gums and polymers. *Polimery w Medycynie,* 41(4), 73-80.

Singh, N., (2007). Configuration of crosslinked multi-polymeric multi-units for site-specific delivery of nicotine (Doctoral dissertation, Department of Pharmacy and Pharmacology, University of the Witwatersrand).

Soller, E. C., Tzeranis, D. S., Miu, K., So, P. T., and Yannas, I. V., (2012). Common features of optimal collagen scaffolds that disrupt wound contraction and enhance regeneration both in peripheral nerves and in skin. *Biomaterials,* 33, 4783-4791.

Tanaka, Y., Kuwabara, R., Na, Y. H., Kurokawa, T., Gong, J. P., and Osada, Y., (2005). Determination of fracture energy of high strength double network hydrogels. *The Journal of Physical Chemistry B,* 109(23), 11559-11562.

Verma, A., and Pandit, J. K., (2012). Comparative evaluation of $Ca^{++}$ and $Zn^{++}$ cross-linked gellan gum based floating beads. *Archives Des Sciences,* 65(2).

Yao, K., Li, J., Yao, F., and Yin, Y., (2011). Chitosan-based hydrogels: functions and applications. CRC Press.

Zhang, H., Alsarra, I. A., and Neau, S. H., (2002). An in vitro evaluation of a chitosan-containing multiparticulate system for macromolecule delivery to the colon. *International Journal of Pharmaceutics,* 239(1), 197-205.

The invention claimed is:

1. A biodegradable implant comprising a hydrogel carrier matrix having dispersed therein a multitude of spheroidal particles, each spheroidal particle including a crosslinked cationic chitosan (CHT) having dispersed therein anionic poly(methacrylic-co-methyl methacrylate) (PMMA) nanoparticles, and wherein the hydrogel carrier matrix comprises at least one anionic polysaccharide.

2. The biodegradable implant according to claim 1, wherein each of the spheroidal particles includes dispersed therein a first active pharmaceutical ingredient (API).

3. The biodegradable implant according to claim 2, wherein the spheroidal particles each includes an outer shell including a chitosan (CHT) poly(methacrylic-co-methyl methacrylate) (PMMA) polyelectrolyte complex (CHT-PMMA-PEC) and an inner core including crosslinked chitosan having dispersed therein PMMA nanoparticles.

4. The biodegradable implant according to claim 3, wherein the outer shell of CHT-PMMA-PEC is formed in situ when the spheroidal particles contact an aqueous medium providing constant release of the first API therefrom.

5. The biodegradable implant according to claim 4, wherein the outer shell of CHT-PMMA-PEC and/or the inner core includes pores.

6. The biodegradable implant according to claim 5, wherein the pores are formed in situ when the outer shell and/or the inner core contacts an aqueous medium of pH between 5 and 9 therein dissolving the PMMA to provide pores, which pores provide for facilitating dissolution of the first API out of the spheroidal particle.

7. The biodegradable implant according to claim 2, wherein the hydrogel carrier matrix further includes a second active pharmaceutical ingredient (API).

8. The biodegradable implant according to claim 7, wherein the first API and the second API is the same API or alternatively different APIs.

9. The biodegradable implant according to claim 1, wherein the at least one anionic polysaccharide includes xanthan gum and gellan gum forming a xanthan gum-gellan gum blend.

10. The biodegradable implant according to claim 9, wherein the hydrogel carrier matrix further comprises a crosslinking agent forming a crosslinked xanthan gum-gellan gum matrix.

11. The biodegradable implant according to claim 1, wherein the hydrogel carrier matrix further includes poly (methacrylic-co-methyl methacrylate) (PMMA) nanoparticles.

12. The biodegradable implant according to claim 11, wherein the hydrogel carrier matrix includes pores.

13. The biodegradable implant according to claim 12, wherein the pores are formed in situ when the hydrogel carrier matrix contacts an aqueous medium of pH between 5 and 9 therein dissolving PMMA to provide pores.

* * * * *